United States Patent
Rothenberg et al.

(10) Patent No.: US 6,355,425 B1
(45) Date of Patent: Mar. 12, 2002

(54) MUTATIONS ASSOCIATED WITH IRON DISORDERS

(75) Inventors: Barry E. Rothenberg, Delmar; Ritsuko Sawada-Hirai, San Diego, both of CA (US); James C. Barton, Birmingham, AL (US)

(73) Assignee: Billups-Rothenberg, Inc., San Diego, CA (US)

(*) Notice: Subject to any disclaimer, the term of this patent is extended or adjusted under 35 U.S.C. 154(b) by 0 days.

(21) Appl. No.: 09/277,457

(22) Filed: Mar. 26, 1999

(51) Int. Cl.[7] .......................... C12Q 1/68; C07H 21/02

(52) U.S. Cl. .................................. 435/6; 536/22.1

(58) Field of Search ................... 435/6, 91.2; 536/22.1, 536/23.1

(56) References Cited

U.S. PATENT DOCUMENTS

| | | | |
|---|---|---|---|
| 4,946,778 A | 8/1990 | Ladner et al. | 435/69.6 |
| 5,705,343 A | 1/1998 | Drayna et al. | 435/6 |
| 5,712,098 A | 1/1998 | Tsuchihashi et al. | 435/6 |
| 5,877,015 A | 3/1999 | Hardy et al. | 435/325 |
| 5,879,892 A | 3/1999 | Van Baren et al. | 435/6 |
| 5,879,904 A | 3/1999 | Brechot et al. | 435/69.1 |
| 5,879,908 A | 3/1999 | Laping et al. | 435/69.1 |

FOREIGN PATENT DOCUMENTS

| | | | |
|---|---|---|---|
| WO | WO 98/14466 | 4/1998 | C07H/21/04 |

OTHER PUBLICATIONS

Beutler, et al., "HLA–H and Associated Proteins in Patients with Hemochromatosis" *Mol. Med.*, vol. 3, No. 6, pp. 397–402 (Jun. 1997).

Douabin et al., "Polymorphisms in the HFE Gene" *Hum. Hered.*, vol. 49, No. 1, pp. 21–26 (Jan. 1999).

Sanchez et al., Prevalence of the Cys282Tyr and His63Asp HFE gene mutations in Spanish patients with hereditary hemochromatosis and in controls; Journal of Hepatology 1998; pp. 725–728.

Wenz et al.; A rapid automated SSCP multiplex capillary electrophoresis protocol that detects the two common mutations implicated in hereditary hemochromatosis (HH); Hum. Genet., vol. 104, No. 1, 1999; pp. 29–35.

Bernard et al., Homogeneous Multiplex Genotyping of Hemochromatosis Mutations with Fluorescent Hybridization Probes, Am. J. Pathology, vol. 153, No. 4, Oct., 1998. pp. 1055–1061.

Mura et al., HFE Mutations Analysis in 711 Hemochromatosis Probands: Evidence for S65C Implication In Mild Form of Hemochromatosis; BLOOD, vol. 93, No. 8, 1999. pp. 2502–2505.

Barton et al., Two Novel Missense Mutations of the HFE Gene (I105T and G93R) and Identification of the S65C Mutation in Alabama Hemochromatosis Probands, Blood Cells, Molecules, and Diseases, vol. 25, No. 9, 1999. pp. 147–155.

Sosnowski et al., Rapids determination of single base mismatch mutations in DNA hybrids by direct electic field control, Proc. Natl. Acad. Sci. USA, vol. 94, pp. 1119–1123, Feb. 1997.

Edman et al., Electic field directed nucleic acid hybridization on microchips, Nucleic Acids Research, 1997, vol. 25, No. 24, pp. 4907–4914.

Cheng et al., Prepartion and hybridization analysis of DNA/RNA from *E. coli* on microfabricated bioelectric chips, Nature Biotechnology, vol. 16, pp. 541–546, Jun. 1998.

Lebron et al., "Crystal Structure of the Hemochromatosis Protein HFE and Characterization of Its Interaction with Transferrin Receptor", vol. 93, 111–123, Apr. 3, 1998.

Bjorkman et al., "The foreign antigen binding site and T cell recognition regions of class I histocompatibility antigens", Nature vol. 329, Oct. 8, 1987.

Fargion et al., "Genetic Hemochromatosis in Italian patients with porphyria cutanea tarda", Journal of Hepatology 1996; 24:564–569.

Bulaj et al., "Clinical and Biochemical Abnormalties in People Heterozygous for Hemochromatosis", N.E. Journal of Medicine, Dec. 1996, vol. 335, No. 24, pp. 1799–1805.

Roberts et al., "The Frequency of Hemochromatosis–Associated Alleles Is Increased in British Patients With Sporadic Porphyria Cutanea Tarda", Hepatology vol. 25, No. 1, 1997, pp. 159–161.

Roberts et al, "Increased frequency of the haemochromatosis Cys282Tyr mutation in sporadic porphyria cutanea tarda", The Lancet 1997; 349: 321–23.

O'Reilly et al., "Screening of Patients With Iron Overloan to Identify Hemochromatosis and Porphyria Cutanea Tarda", Arch Dermatol/vol. 133, Sep. 1997 pp. 1098–1101.

Sampietro et al., "High Prevalence of the His63Asp HPE Mutation in Italian Patients With Porphyria Cutanea Tarda", Hepatology vol. 27, No. 1, 1998.

Lefkowitch, MD, "Iron–Rich Foci in Chronic Viral Hepatitis", Human Pathology, vol. 29, No. 2 Feb. 1998 pp. 116–118.

Mark Worwood, "Revisiting various iron overload syndromes after the haemochromatosis gene discovery", Journal of Hepatology, 1998; 28: 26–27.

Stuart et al., "The C282Y mutation in the haemochromatosis gene (HFE) and hepatitis C virus infection are independent cofactors for porphyria . . . ", Jour. of Hepatology, 1998; 28: 404–409.

(List continued on next page.)

Primary Examiner—Eggerton Campbell
(74) Attorney, Agent, or Firm—Mintz Levin Cohn Ferris Glovsky and Popeo, P.C.; Ingrid Beattie, Ph.D.

(57) ABSTRACT

The invention features a method of diagnosing an iron disorder, e.g., hemochromatosis, or a genetic susceptibility to developing such a disorder in a mammal by determining the presence of a mutation in exon 2 or in an intron of an HFE nucleic acid.

53 Claims, 3 Drawing Sheets

OTHER PUBLICATIONS

Bonkovsky et al., "Porphyria Cutanea Tarda, Hepatitis C, and HFE Gene Mutations in North America", Hepatology Jun. 1998; vol. 27, No. 6, pp. 1661–1669.

Mendez et al., "Familial Porphyria Cutanea Tarda: Characterization of Seven Novel Uroporphyrinogen . . . ", Am. J. Hum. Genet. 63:1363–1375, 1998.

Agnes et al., "Strongly increased effeciency of altered peptide ligands by mannosylation", International Immunology, vol. 10, No. 9 pp. 1299–1304, 1998.

Walter Gerhard, "Fusion of Cells in Suspension and Outgrowth of Hybrids in Conditioned Medium", Plenum Press, Fusion Protocols, pp. 370–371, 1980.

Kohler et al., "Continuous cultures of fused cells secreting antibody of predefined specificity", Nature vol. 256, Aug. 7, 1975 pp. 495–497.

Ghose et al., "Strategy for Linkage of Cytotoxic Agents", Methods in Ezzymology, vol. 93, 1983, 1983. pp. 281–333.

Feder et al., "The Hemochromatosis Founder Mutation in HLA–H Disrupts . . . ", Journal of Biological Chemistry vol. 272, No. 22, pp. 14025–14028, 1997.

Edman et al., "Electric field directed nucleic acid hybidiaztion on microchips", Nucleic Acids Research, 1997, vol. 25, No. 24, 1997.

Cheng et al., "Preparation and hybridization analysis on DNA/RNA from *E. coli* microfabricated bioelectronic chips", Nature Biotechnology, vol. 16, No. 6, Jun. 1998, pp. 541–546.

Bernard et al., "Homogeneious Multiplex Genotyping of Hemochromatosis Mutations with Fluorescent Hybridization Probes", American Journal of Pathology, vol. 153, No. 4, 1998.

Nikiforov et al., Genetic Bit Analysis: a solid phase method for typing signle nucleotide polymorphisms Nucleic Acids Research, 1994, vol. 22, No. 2 4167–4175.

Rust et al., "Mutagenically separated PCR (MS–PCR): a highly specific one step procedure for easy mutation detection", Nucleic Acids Research, 1993, vol. 21, No. 16 3623–3629.

Nickerson et al. "Automated DNA diagnostic using an ELISA–based oligonucleotide ligation assay", Proc. Natl. Acad. Sci. USA, vol. 87, pp. 8923–8927, 1990.

Clevers et al., "Mutations of the hereditary hemochromatosis candidate gene HLA–H in porphyria cutanea tarda" N. Engl. Med 1997 May 1;336(18):1327–8.

MUTATIONS ASSOCIATED WITH IRON DISORDERS

BACKGROUND OF THE INVENTION

Hemochromatosis is the most common progressive (and sometimes fatal) genetic disease in people of European descent. Hemochromatosis is a disease state characterized by an inappropriate increase in intestinal iron absorption. The increase can result in deposition of iron in organs such as the liver, pancreas, heart, and pituitary. Such iron deposition can lead to tissue damage and functional impairment of the organs.

In some populations, 60–100% of cases are attributable to homozygosity for a missense mutation at C282Y in the Histocompatibility iron (Fe) loading (HFE) gene, a major histocompatibility (MHC) non-classical class I gene located on chromosome 6p. Some patients are compound heterozygotes for C282Y and another mutation at H63D.

SUMMARY OF THE INVENTION

The invention is based on the discovery of novel mutations which are associated with aberrant iron metabolims, absorption, or storage, or in advanced cases, clinical hemochromatosis. Accordingly, the invention features a method of diagnosing an iron disorder, e.g., hemochromatosis or a genetic susceptibility to developing such a disorder, in a mammal by determining the presence of a mutation in exon 2 of an HFE nucleic acid. The mutation is not a C→G missense mutation at position 187 of SEQ ID NO:1 which leads to a H63D substitution. The nucleic acid is an RNA or DNA molecule in a biological sample taken from the mammal, e.g. a human patient, to be tested. The presence of the mutation is indicative of the disorder or a genetic susceptibility to developing it. An iron disorder is characterized by an aberrant serum iron level, ferritin level, or percent saturation of transferrin compared to the level associated with a normal control individual. An iron overload disorder is characterized by abnormally high iron absorption compared to a normal control individual. Clinical hemochromatosis is defined by an elevated fasting transferrin saturation level of greater than 45% saturation.

For example, the mutation is a missense mutation at nucleotide 314 of SEQ ID NO:1 such as 314C which leads to the expression of mutant HFE gene product with amino acid substitution I105T. The I105 T mutation is located in the α1 helix of the HFE protein and participates in a hydrophobic pocket (the "F" pocket). The alpha helix structure of the α1 domain spans residues S80 to N108, inclusive. The I105T mutation is associated with an iron overload disorder.

TABLE 1

Human HFE cDNA sequence atgggccg cgagccaggc cggcgcttct cctcctgatg cttttgcaga ccgcggtcct gcagggcgc ttgctgcgtt cacactctct gcactacctc ttcatgggtg cctcagagca ggaccttggt ctttccttgt ttgaagcttt gggctacgtg gatgaccagc tgttcgtgtt ctatgat<u>cat</u> gag<u>agt</u>cgcc
                                                                                                  H63D     S65C gtgtggagcc ccgaactcca tgggtttcca gtagaatttc aagccagatg tggctgcagc tgagtcagag tctgaaa<u>ggg</u> tgggatcaca tgttcactgt tgacttctgg act<u>att</u>atgg
                                      G93R                                                                        I105T aaaatcacaa ccacagcaag gagtcccaca ccctgcaggt catcctgggc tgtgaaatgc aagaagacaa cagtaccgag ggctactgga agtacgggta tgatgggcag gaccaccttg aattctgccc tgacacactg gattggagag cagcagaacc cagggcctgg cccaccaagc tggagtggga aaggcacaag attcgggcca ggcagaacag ggcctacctg gagagggact gccctgcaca gctgcagcag ttgctggagc tggggagagg tgttttggac caacaagtgc ctcctttggt gaaggtgaca catcatgtga cctcttcagt gaccactcta cggtgtcggg ccttgaacta ctaccccag aacatcacca tgaagtggct gaaggataag cagccaatgg atgccaagga gttcgaacct aaagacgtat tgcccaatgg ggatgggacc taccagggct ggataaccctt ggctgtaccc cctggggaag agcagagata tacgtgccag gtggagcacc caggcctgga tcagcccctc attgtgatct gggagccctc accgtctggc accctagtca ttggagtcat cagtggaatt gctgttttg tcgtcatctt gttcattgga attttgttca taatattaag gaagaggcag ggttcaagag gagccatggg gcactacgtc ttagctgaac gtgagtgaca cgcagcctgc agactcactg tgggaaggag acaaaactag agactcaaag agggagtgca tttatgagct cttcatgttt caggagagag ttgaacctaa acatagaaat tgcctgacga actccttgat tttagccttc tctgttcatt tcctcaaaaa gatttcccca tttaggtttc tgagttcctg catgccggtg atccctagct gtgacctctc ccctggaact

TABLE 1-continued

Human HFE cDNA sequence

```
gtctctcatg aacctcaagc tgcatctaga ggcttccttc atttcctccg tcacctcaga
gacatacacc tatgtcattt catttcctat ttttggaaga ggactcctta aatttggggg
acttacatga ttcattttaa catctgagaa aagctttgaa ccctgggacg tggctagtca
taaccttacc agattttac acatgtatct atgcattttc tggacccgtt caacttttcc
tttgaatcct ctctctgtgt tacccagtaa ctcatctgtc accaagcctt ggggattctt
ccatctgatt gtgatgtgag ttgcacagct atgaaggctg tgcactgcac gaatggaaga
ggcacctgtc ccagaaaaag catcatggct atctgtgggt agtatgatgg gtgttttag
caggtaggag gcaaatatct tgaaaggggt tgtgaagagg tgttttttct aattggcatg
aaggtgtcat cacgatttgc aaagtttaat ggtgccttca tttgggatgc tactctagta
ttccagacct gaagaatcac aataattttc tacctggtct ctccttgttc tgataatgaa
aattatgata aggatgataa aagcacttac ttcgtgtccg actcttctga gcacctactt
acatgcatta ctgcatgcac ttcttacaat aatttatga gataggtact attatccccca
tttcttttt aaatgaagaa agtgaagtag gccgggcacg gtggctcgcg cctgtggtcc
cagggtgctg agattgcagg tgtgagccac cctgcccagc cgtcaaaaga gtcttaatat
atatatccag atggcatgtg tttacttat gttactacat gcacttggct gcataaatgt
ggtacaacca ttctgtcttg aagggcaggt gcttcaggat accatataca gctcagaagt
ttcttcttta ggcattaaat tttagcaaag atatctcatc tcttctttta aaccattttc
tttttttgtg gttagaaaag ttatgtagaa aaagtaaat gtgatttacg ctcattgtag
aaaagctata aaatgaatac aattaaagct gttatttaat tagccagtga aaaactatta
acaacttgtc tattacctgt tagtattatt gttgcattaa aaatgcatat actttaataa
atgtacattg tattgtaaaa aaaaaaa
```

(SEQ ID NO:11 GENBANK® Accession No. U60319)

TABLE 2

Human HFE gene product

MGPRARPALLLLMLLQTAVLQG

RLLRSHSLHYLFMGASEQDLGLSLFEALGYVDDQLFVFYDHESRRVEPRTPWVSSISSQ

MWLQLSQSLKGWDHMFTVDFWTIMENHNHSKESHTLQVILGCEMQEDNSTEGYWKYGYDG

QDHLEFCPDTLDWRAAEPRAWPTKLEWERHKIRARQNRAYLERDCPAQLQQLLELGRGVL

DQQVPPLVKVTHHVTSSVTTLRCRALNYYPQNITMKWLKDKQPMDAKEFEPKDVLPNGDG

TYQGWITLAVPPGEEQRYTCQVEHPGLDQPLIVIWEPSPSGTLVIGVISGIAVFVVILFI

GILFIILRKRQGSRGAMGHYVLAERE (SEQ ID NO: 2; GENBANK ® Accession

No. U60319)

Residues 1–22=leader sequence; α1 domain underlined; residues 63, 65, 93, and 105 indicated in bold type)

Other mutations include nucleotide 277 of SEQ ID NO:1, e.g., 277C which leads to expression of mutant HFE gene product G93R and one at nucleotide 193 of SEQ ID NO:1, e.g., 193T, which leads to expression of mutant HFE gene product S65C.

Any biological sample containing an HFE nucleic acid or gene product is suitable for the diagnostic methods described herein. For example, the biological sample to be analyzed is whole blood, cord blood, serum, saliva, buccal tissue, plasma, effusions, ascites, urine, stool, semen, liver tissue, kidney tissue, cervical tissue, cells in amniotic fluid, cerebrospinal fluid, hair or tears. Prenatal testing can be done using methods used in the art, e.g., amniocentesis or chorionic villa sampling. Preferably, the biological sample is one that can be non-invasively obtained, e.g., cells in saliva or from hair follicles.

The assay is also used to screen individuals prior to donating blood to blood banks and to test organ tissue, e.g., a donor liver, prior to transplantation into a recipient patient. Both donors and recipients are screened.

In some cases, a nucleic acid is amplified prior to detecting a mutation. The nucleic acid is amplified using a first oligonucleotide primer which is 5' to exon 2 and a second oligonucleotide primer is 3' to exon 2. To detect mutation at nucleotide 314 of SEQ ID NO:1, a first oligonucleotide primer which is 5' to nucleotide 314 and a second oligonucleotide primer which is 3' to nucleotide 314 is used in a standard amplification procedure such as polymerase chain reaction (PCR). To amplify a nucleic acid containing nucleotide 277 of SEQ ID NO:1, a first oligonucleotide primer which is 5' to nucleotide 277 and a second oligonucleotide primer which is 3' to nucleotide 277 is used. Similarly, a nucleic acid containing nucleotide 193 of SEQ ID NO:1 is amplified using primers which flank that nucleotide. For example, for nucleotide 277, the first primer has a nucleotide sequence of SEQ ID NO:3 and said second oligonucleotide primer has a nucleotide sequence of SEQ ID NO:4, or the first primer has a nucleotide sequence of SEQ ID NO:15 and said second oligonucleotide primer has a nucleotide sequence of SEQ ID NO:16. Table 3, below, shows examples of primer pairs for amplification of nucleic acids in exons and introns of the HFE gene.

out to produce a mature RNA product, i.e., a mRNA, which is then transported to the cytoplasm. A method of diagnosing an iron disorder or a genetic susceptibility to developing the disorder is carried out by determining the presence or absence of a mutation in an intron of HFE genomic DNA in a biological sample. The presence of the mutation is indicative of the disorder or a genetic susceptibility to developing the disorder. The presence of a mutation in an intron is a marker for an exon mutation, e.g., a mutation in intron 4, e.g., at nucleotide 6884 of SEQ ID NO:27 is associated with the S65C mutation in exon 2. A mutation in intron 5, e.g., at nucleotide 7055 of SEQ ID NO:27 is associated with hemochromatosis. In some cases, intron mutations may adversely affect proper splicing of exons or may alter regulatory signals. Preferably, the intron 4 mutation is 6884C and the intron 5 mutation is 7055G. To amplify nucleic acid molecule containing nucleotide 6884 or 7055, primers which flank that nucleotide, e.g., those described in Table 3, are used according to standard methods. Nucleic acid-based diagnostic methods may or may not include a step of amplification to increase the number of copies of the nucleic acid to be analyzed. To detect a mutation in intron 4, a patient-derived nucleic acid may be amplified using a first oligonucleotide primer which is 5' to intron 4 and a second oligonucleotide primer which is 3' to intron 4, and to detect a mutation in intron 5, the nucleic acid may be amplified using a first oligonucleotide primer which is 5' to intron 5 and a second oligonucleotide primer which is 3' to intron 5 (see, e.g., Table 3).

TABLE 3

| Target DNA | Forward Primer | Reverse Primer |
|---|---|---|
| I. PRIMERS USED FOR AMPLIFICATON | | |
| Exon 2 | CCTCCTACTACACATGGTTAGG (SEQ ID NO: 3) | GCTCTGACAACCTCAGGAAGG (SEQ ID NO: 4) |
| Exon 3 | GGTGGAAATAGGGACCTATTCC (SEQ ID NO: 5) | CACTCTGCCACTAGACTATAGG (SEQ ID NO: 6) |
| Exon 4 | GGTCCAGTCTTCCTGGCAAGG (SEQ ID NO: 7) | AAATGCTTCCCATGGATGCCAG (SEQ ID NO: 8) |
| RT-PCR | AAAGGATCCACCATGGGCCCGCGAGCCAGG (SEQ ID NO: 9) | GTGAGTCTGCAGGCTGCGTG (SEQ ID NO: 10) |
| Intron 4 | GTTCCAGTCTTCCTGGCAAGG (SEQ ID NO: 11) | AAATGCTTCCCATGGATGCCAG (SEQ ID ND: 12) |
| Intron 5 | GTTCCAGTCTTCCTGGCAAGG (SEQ ID NO: 13) | AAATGCTTCCCATGGATGCCAG (SEQ ID NO: 14) |
| II. PRIMERS USED FOR AMPLIFICATION | | |
| Exon 2 | GTGTGGAGCCTCAACATCCTG (SEQ ID NO: 15) | ACAAGACCTCAGACTTCCAGC (SEQ ID NO: 16) |
| Exon 3 | GGTGGAAATAGGGACCTATTCC (SEQ ID NO: 17) | CACTCTGCCACTAGAGTATAGG (SEQ ID NO: 18) |
| Exon 4 | GTTCCAGTCTTCCTGGCAAGG (SEQ ID ND: 19) | TTACCTCCTCAGGCACTCCTC (SEQ ID ND: 20) |
| RT- PCR | AAAGGATCCACCATGGGCCCGCGAGCCAGG (SEQ ID NO: 21) | GTGAGTCTGCAGGCTGCGTG (SEQ ID NO: 22) |
| Intron 4 | TGCCTGAGGAGGTAATTATGG (SEQ ID ND: 23) | AAATGCTTCCCATGGATGCCAG (SEQ ID NO: 24) |
| Intron 5 | TGCCTGAGGAGGTAATTATGG (SEQ ID NO: 25) | AAATGCTTCCCATGGATGCCAG (SEQ ID NO: 26) |

Mutations in introns of the HFE gene have now been associated with iron disorders and/or hemochromatosis. By "exon" is meant a segment of a gene the sequence of which is represented in a mature RNA product, and by "intron" is meant a segment of a gene the sequence of which is not represented in a mature RNA product. An intron is a part of a primary nuclear transcript which is subsequently spliced In addition to nucleic acid-based diagnostic methods, the invention includes a method of diagnosing an iron overload disorder or a genetic susceptibility thereto by determining the presence of a mutation in a HFE gene product in a biological sample. For example, the mutation results in a decrease in intramolecular salt bridge formation in the mutant HFE gene product compared to salt bridge formation in a wild type HFE gene product. The mutation which affects salt bridge formation is at or proximal to residue 63 of SEQ ID NO:2, but is not amino acid substitution H63D. Preferably, the mutation is between residues 23–113, inclusive of SEQ ID NO:2 (Table 2), more preferably, it is between residues 90–100, inclusive, of SEQ ID NO:2, more preferably, it is between residues 58–68, inclusive, of SEQ ID NO:2, and most preferably, the mutation is amino acid substitution S65C. Alternatively, the mutation which affects salt bridge formation is a mutation, e.g., an amino acid substitution at residue 95 or proximal to residue 95 of SEQ ID NO:2. Preferably, the mutation is G93R. Such an HFE mutation is detected by immunoassay or any other ligand binding assay such as binding of the HFE gene product to a transferrin receptor. Mutations are also detected by amino acid sequencing, analysis of the structural conformation of the protein, or by altered binding to a carbohydrate or peptide mimetope.

A mutation indicative of an iron disorder or a genetic susceptibility to developing such a disorder is located in the α1 helix (e.g., which spans residues 80–108, inclusive, of SEQ ID NO:2) of an HFE gene product. The mutation may be an addition, deletion, or substitution of an amino acid in the wild type sequence. For example, the mutant HFE gene product contains the amino acid substitution I105T or G93R or in the loop of the β sheet of the HFE molecule, e.g., mutation S65C Isolated nucleic acids encoding a mutated HFE gene products (and nucleic acids with nucleotide sequences complementary to such coding sequences) are also within the invention. Also included are nucleic acids which are at least 12 but less than 100 nucleotides in length. An isolated nucleic acid molecule is a nucleic acid molecule that is separated from the 5' and 3' sequences with which it is immediately contiguous in the naturally occurring genome of an organism. "Isolated" nucleic acid molecules include nucleic acid molecules which are not naturally occurring. For example, an isolated nucleic acid is one that has been amplified in vitro, e.g, by PCR; recombinantly produced; purified, e.g., by enzyme cleavage and gel separation; or chemically synthesized. For example, the restriction enzyme, Bst4C I (Sib Enzyme Limited, Novosibirsk, Russia), can be used to detect the G93R mutation (point mutation 277C); this enzyme cuts the mutated HFE nucleic acid but not the wild type HFE nucleic acid. Such nucleic acids are used as markers or probes for disease states. For example, a marker is a nucleic acid molecule containing a nucleotide polymorphism, e.g., a point mutation, associated with an iron disorder disease state flanked by wild type HFE sequences. The invention also encompasses nucleic acid molecules that hybridize, preferably under stringent conditions, to a nucleic acid molecule encoding a mutated HFE gene product (or a complementary strand of such a molecule). Preferably the hybridizing nucleic acid molecule is 400 nucleotides, more preferably 200 nucleotides, more preferably 100, more preferably 50, more preferably 25 nucleotides, more preferably 20 nucleotides, and most preferably 10–15 nucleotides, in length. For example, the nucleotide probe to detect a mutation is 13–15 nucleotides long. The nucleic acids are also used to produce recombinant peptides for generating antibodies specific for mutated HFE gene products. In preferred embodiments, an isolated nucleic acid molecule encodes an HFE polypeptide containing amino acid substitution I105T, G93R, or S65C, as well as nucleic acids the sequence of which are complementary to such nucleic acid which encode a mutant or wild type HFE gene product.

Also within the invention are substantially pure mutant HFE gene products, e.g., an HFE polypeptide containing amino acid substitution I105T, G93R, or S65C. Substantially pure or isolated HFE polypeptides include those that correspond to various functional domains of HFE or fragments thereof, e.g., a fragment of HFE that contains the α1 domain.

Wild type HFE binds to the transferrin receptor and regulates the affinity of transferrin receptor binding to transferrin. For example, a C282Y mutation in the HFE gene product reduces binding to the transferrin receptor, thus allowing the transferrin receptor to bind to transferrin (which leads to increased iron absorption).

The polypeptides of the invention encompass amino acid sequences that are substantially identical to the amino acid sequence shown in Table 2 (SEQ ID NO:2). Polypeptides of the invention are recombinantly produced, chemically synthesized, or purified from tissues in which they are naturally expressed according to standard biochemical methods of purification. Biologically active or functional polypeptides are those which possess one or more of the biological functions or activities of wild type HFE, e.g., binding to the transferrin receptor or regulation of binding of transferrin to the transferrin receptor. A functional polypeptide is also considered within the scope of the invention if it serves as an antigen for production of antibodies that specifically bind to an HFE epitope. In many cases, functional polypeptides retain one or more domains present in the naturally-occurring form of HFE.

The functional polypeptides may contain a primary amino acid sequence that has been altered from those disclosed herein. Preferably, the cysteine residues in exons 3 and 4 remain unchanged. Preferably the modifications consist of conservative amino acid substitutions. The terms "gene product", "protein", and "polypeptide" are used herein to describe any chain of amino acids, regardless of length or post-translational modification (for example, glycosylation or phosphorylation). Thus, the term "HFE polypeptide or gene product" includes full-length, naturally occurring HFE protein, as well a recombinantly or synthetically produced polypeptide that correspond to a full-length naturally occurring HFE or to a particular domain or portion of it.

The term "purified" as used herein refers to a nucleic acid or peptide that is substantially free of cellular material, viral material, or culture medium when produced by recombinant DNA techniques, or chemical precursors or other chemicals when chemically synthesized. Polypeptides are said to be "substantially pure" when they are within preparations that are at least 60% by weight (dry weight) the compound of interest. Preferably, the preparation is at least 75%, more preferably at least 90%, and most preferably at least 99%, by weight the compound of interest. Purity can be measured by any appropriate standard method, for example, by column chromatography, polyacrylamide gel electrophoresis, or HPLC analysis.

Diagnostic kits for identifying individuals suffering from or at risk of developing an iron disorder are also within the invention. A kit for detecting a nucleotide polymorphism associated with an iron disorder or a genetic susceptibility thereto contains an isolated nucleic acid which encodes at least a portion of the wild type or mutated HFE gene product, e.g., a portion which spans a mutation diagnostic for an iron disorder or hemochromatosis (or a nucleic acid the sequence of which is complementary to such a coding sequence). A kit for the detection of the presence of a mutation in exon 2 of an HFE nucleic acid contains a first oligonucleotide primer which is 5' to exon 2 and a second oligonucleotide primer is 3' to exon 2, and a kit for an antibody-based diagnostic assay includes an antibody which preferentially binds to an epitope of a mutant HFE gene product, e.g., an HFE polypeptide containing amino acid substitution I105T, G93R, or S65C, compared to its binding to the wild type HFE polypeptide. An increase in binding of the mutant HFE-specific antibody to a patient-derived sample (compared to the level of binding detected in a wild type sample or sample derived from a known normal control individual) indicates the presence of a mutation which is diagnostic of an iron disorder, i.e., that the patient from which the sample was taken has an iron disorder or is at risk of developing one. The kit may also contain an antibody which binds to an epitope of wild type HFE which contains residue 105, 93, or 65. In the latter case, reduced binding of the antibody to a patient-derived HFE gene product (compared to the binding to a wild type HFE gene product or a gene product derived from a normal control individual) indicates the presence of a mutation which is diagnostic of an iron disorder, i.e., that the patient from which the sample was taken has an iron disorder or is at risk of developing one.

Individual mutations and combinations of mutations in the HFE gene are associated with varying severity of iron disorders. For example, the C282Y mutation in exon 4 is typically associated with clinical hemochromatosis, whereas other HFE mutations or combinations of mutations in HFE nucleic acids are associated with disorders of varying prognosis. In some cases, hemochromatosis patients have been identified which do not have a C282Y mutation. The I105T and G93R mutations are each alone associated with an increased risk of iron overload (compared to, e.g., the H63D mutational one), and the presence of both the I105T and H63D mutation is associated with hemochromatosis. Accordingly, the invention includes a method of determining the prognosis for hemochromatosis in a mammal suffering from or at risk of developing said hemochromatosis by (a) detecting the presence or absence of a first mutation in exon 4 in each allele of an HFE nucleic acid, e.g., patient-derived chromosomal DNA, and (b) detecting the presence of a second mutation in exon 2 in each allele of the nucleic acid. The presence of the first mutation in both chromosomes, i.e. an exon 4 homozygote such as a C282Y homozygote, indicates a more negative prognosis compared to the presence of the second mutation in one or both chromosomes, i.e., an exon 2 heterozygote or homozygote. An exon 4 mutation homozygote is also associated with a more negative prognosis compared to the presence of a first mutation (exon 4) in one allele and the presence of the second mutation (exon 2) in one allele, i.e., a compound heterozygote.

Other features and advantages of the invention will be apparent from the following detailed description, and from the claims.

DETAILED DESCRIPTION

Figure 1:
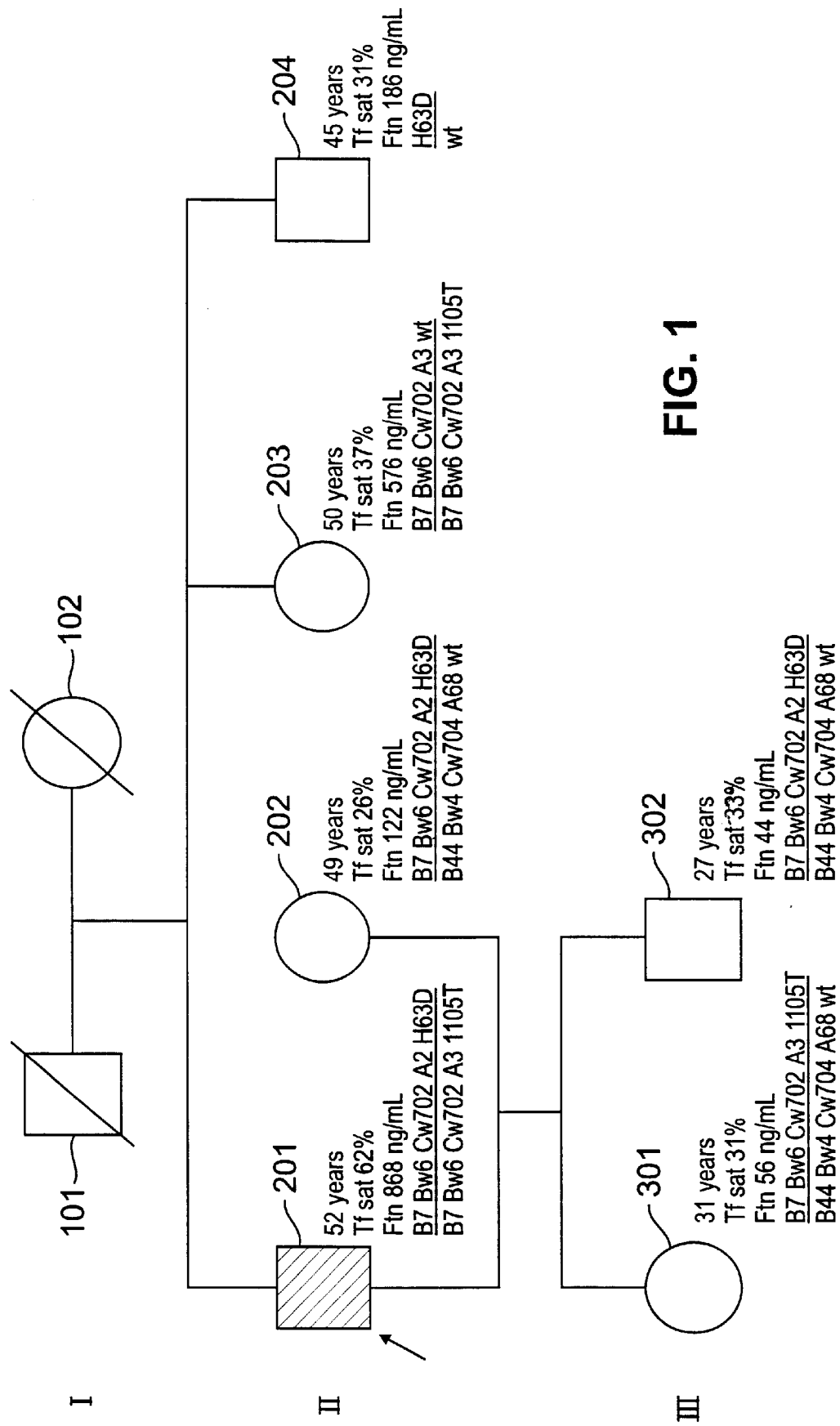
FIG. 1 is a diagram of the family of proband 1 (HFE genotype H63D/I105T). □=male, ●=female, Ø=deceased, ■=hemochromatosis phenotype. Proband 1 is indicated by an arrow. Phenotype and genotype data: age in year saturation; % Ftn=serum ferritin concentration. I105 separate chromosomes. The sister of the proband (II, 203) has hyperferritinemia.

A proband is the first individual in a family identified to be affected by hemochromatosis. Forward and reverse sequencing of HFE exons 2, 3, 4, and 5, and of portions of HFE introns 2, 4, and 5 was carried out on biological samples taken from twenty hemochromatosis probands who lacked C282Y homozygosity, C282Y/H63D compound heterozygosity, or H63D homozygosity. Four probands had novel HFE coding region mutations. Probands 1 and 2 were heterozygous for previously undescribed mutations: exon 2, nt 314T→C (314C; I105T), and exon 2, nt 277G→C (277C; G93R), respectively; these probands were also heterozygous for H63D and C282Y, respectively. Probands 3 and 4 were heterozygous for an HFE mutation in exon 2, nt 193A→T (193T; S65C). Twelve other probands did not have an exon 2 HFE exon mutation; four were heterozygous for H63D. In probands 1, 2, 3, and 4, the amino acid substitutions I105T, G93R, and S65C (respectively) occurred on separate chromosomes from those with the C282Y or H63D mutations. In 176 normal control subjects, two were heterozygous for S65C; I105T and G93R were not detected in controls. Nine probands were heterozygous and two probands were homozygous for a base-pair change at intron 2, nt 4919T/C (SEQ ID NO:27). Heterozygosity for a base-pair change in intron 4 (nt 6884T→C) was detected only in probands 3 and 4, both of whom also had S65C and HLA-A32. The intron 2 mutation is not diagnostic of an iron disorder and appears randomly in the population. One proband was heterozygous for a base-pair change at intron 5 (nt 7055A→G).

The data described herein indicate that, in addition to the C282Y and H63D HFE mutations, the HFE exon and intron 5 mutations described herein are diagnostic (and prognostic) of iron disorders.

Pathology of Iron Overload

Iron plays an essential role in normal growth and development, but in elevated concentrations, iron is a toxic inorganic molecule and is the leading cause of death in children by poisoning. It has been implicated in the pathophysiology of a number of common diseases, e.g., hepatitis, cancer, heart disease, reperfusion injury, rheumatoid arthritis, diabetes, AIDS, and psychological abnormalities (e.g. depression).

The incidence of cancer (especially liver cancer) rises dramatically in the course of hemochromatosis. Iron, acting alone or in synergy with other environmental agents, catalyzes free radical formation. These free radicals which mediate tissue damage also cause DNA double strand breaks and oncogene activation. Iron may also play a role in the pathogenesis of rheumatic diseases and in predisposition to heart disease. High levels of iron can also cause diabetes with 2% of diabetics being hemochromatosis patients. High levels of iron may also affect the disease progression of many viral diseases. Individuals infected with such viruses as hepatitis (e.g., hepatitis B or C) or HIV should be tested for HFE mutations because of the impact increased iron stores have on the treatment and prognosis of such diseases.

Excessive iron stores and iron deposition is also a major contributing factor in the pathology and treatment of nonvalvular heart disease. These conditions include dilated cardiomyopathy cased by deposition of iron in myocardial fibers; myocardial injury the product of anthracycline cardiomyopathy and re-perfusion injury. Increased iron stores may also be a contributing factor in myocardial infarction due to atherosclerosis. Some evidence suggests a significant increase in the incidence of reported heart disease in probands (cardiac symptoms—32%, insulin-dependent diabetes—18%, cardiac arrhythmia—17%, clinically significant coronary artery atherosclerosis—9%, and congestive heart failure—7%. Cardiac complications have been detected in 30% of patients. These include EKG abnormalities, congestive heart failure and cardiac arrhythmias. An increased frequency of HFE mutations in individuals with porphyria cutanea tarda indicates that HFE mutations may predispose an individual to developing this syndrome.

The effect of iron overload is irreparable damage to vital organs and a multiplicity of associated pathologies described above. The multiplicity of clinical symptoms (and associated pathologies) often causes misdiagnosis of hemochromatosis or failure to diagnose hemochromatosis.

Untreated hemochromatosis is characterized by iron overload of parenchymal cells, which is toxic and the probable cause of various complications including cirrhosis, and liver cancer, arthropathy, hypogonadotropic hypogonadism, marrow aplasia, skin disorders, diabetes mellitus, and cardiomyopathy. There are 1.5 to 2 million active cases in the U.S. of which 40% have progressive liver disease because they have not been properly diagnosed or treated.

In untreated hemochromatosis, iron is universally deposited in the hepatocytes of the liver. The iron is found primarily in the cytoplasm of hepatocytes, and by electron microscopy in lysosomal vacuoles, and in more severe cases iron has also been reported deposited in mitochondria. Other liver toxins such as alcohol, and hepatitis exacerbate the damage caused by the iron deposition. Patients with hemochromatosis are advised not to drink, because of increased liver damage, or to smoke, as iron deposition can also occur in the lungs.

Individuals which are homozygous (and to a lesser extent heterozygous) for an HFE mutation are at risk for developing increased levels of blood lead. Thus, it is important to identify heterozygous as well as homozygous patients.

Identification and detection of mutations in the HFE gene are critical to understanding the general mechanisms of iron disorders and diagnosing iron-related pathologies.

Nucleic Acid-based Assays for HFE Mutations

A biological sample containing RNA or DNA is obtained from an individual and the nucleic acid extracted. Optionally, the nucleic acid is amplified according to standard procedures such as PCR. A nucleic acid polymorphism, e.g, a single base pair polymorphism, is detected using methods well known in the art of molecular biology. For example, a mutation is detected using a standard sequencing assay, nucleic acid hybridization, e.g, using standard Southern, Northern, or dot blot hybridization assay systems and an HFE-specific oligonucleotide probe, restriction enzyme fragment polymorphism analysis, oligonucleotide ligation assay (OLA; Nikerson etal., 1990, Nucl. Acids Res. 87:8923–8927), primer extension analysis (Nikiforov etal., 1994, Nucl. Acids Res. 22:4167–4175), single strand conformation polymorphism (SSCP) analysis, allele-specific PCR (Rust etal., 1993, Nucl. Acids Res. 6:3623–3629), denaturing gradient gel electrophoresis (DGGE), fluorescent probe melting curve analysis (Bernard et al., 1998, Am. J. Pathol. 153:1055–61), RNA mismatch cleavage assay, capillary hybridization, or TaqMan™ assay (PE Applied Biosystems, Foster City, Calif.). Nucleic acid hybridization assays are also carried out using a bioelectronic microchip technology known in the art, e.g., that described in Sosnowski etal., 1997, Proc. Natl. Acad. Sci. U.S.A. 94:1119–1123; Cheng etal. 1998, Nature Biotechnology 16:541–546; or Edman etal., 1997, Nucl. Acids Res. 25:4907–4914.

Detection of Mutations using Antibodies and other HFE Ligands

Anti-HFE antibodies are know in the art, e.g., those described by Feder etal., 1997, J. Biol. Chem. 272:14025–14028, or are obtained using standard techniques. Such antibodies can be polyclonal or monoclonal. Polyclonal antibodies can be obtained, for example, by the methods described in Ghose etal., Methods in Enzymology, Vol. 93, 326–327, 1983. An HFE polypeptide, or an antigenic fragment thereof, is used as an immunogen to stimulate the production of HFE-reactive polyclonal antibodies in the antisera of animals such as rabbits, goats, sheep, rodents and the like. HFE antibodies specific for mutated HFE gene products are raised by immunizing animals with a polypeptide spanning the mutation, e.g, a polypeptide which contains the mutations described herein. For example, the entire α1 domain of a mutant HFE gene product is used as an immunogen. Monoclonal antibodies are obtained by the process described by Milstein and Kohler in Nature, 256:495–97, 1975, or as modified by Gerhard, Monoclonal Antibodies, Plenum Press, 1980, pages 370–371. Hybridomas are screened to identify those producing antibodies that are highly specific for an HFE polypeptide containing a mutation characteristic of an iron metabolism abnormality or clinical hemochromatosis. Preferably, the antibody has an affinity of at least about $10^5$ liters/mole, preferably at least $10^6$ liters/mole, more preferably at least $10^8$ liters/mole, and most preferably, an affinity of at least about $10^9$ liters/mole.

Antibodies specific for the wild type HFE can also be used to diagnose hemochromatosis or iron metabolism abnormalities. Such antibodies are also useful research tools to identify novel mutations indicative of iron disorders or hemochromatosis. A reduction in binding to a wild type HFE-specific antibody indicates the presence of a mutation. Antibody binding is detected using known methods. For example, an ELISA assay involves coating a substrate, e.g., a plastic dish, with an antigen, e.g., a patient-derived biological sample containing an HFE gene product. An antibody preparation is then added to the well. Antibodies specific for a mutant HFE gene product bind or fail to bind to a patient-derived sample in the well. Non-binding material is washed away and a marker enzyme e.g., horse radish peroxidase or alkaline phosphatase, coupled to a second antibody directed against the antigen-specific primary antibody is added in excess and the nonadherent material is washed away. An enzyme substrate is added to the well and the enzyme catalyzed conversion is monitored as indicative of presence of the mutation. Antibodies are also labelled with various sizes of colloidal gold particles or latex particles for detection of binding.

The invention employs not only intact monoclonal or polyclonal antibodies, but also an immunologically-active antibody fragment, for example, a Fab or $(Fab)_2$ fragment; an antibody heavy chain, an antibody light chain; a genetically engineered single-chain Fv molecule (Ladner etal., U.S. Pat. No. 4,946,778).

EXAMPLE 1

Selection and Characterization of Subjects

All individuals studied were Caucasians, 18 years of age or older, and from central Alabama. Twenty probands were identified that were either heterozygous for C282Y or H63D, or lacked these mutations. Hemochromatosis is typically diagnosed by detecting elevated saturation of transferrin, with elevated serum ferritin levels, combined with liver biopsy. Each proband patient described below was previously diagnosed to have hemochromatosis by the working diagnostic criterion for hemochromatosis of the American College of Pathologists (elevated fasting transferrin saturation of greater than 60% saturation for males and greater than 50% saturation for females) on at least two occasions in the absence of other known causes. Probands were interviewed regarding their general medical history, diet (including estimated iron content and ethanol consumption), medicinal iron use, receipt of blood transfusion, prior significant hemorrhage, blood donation for transfusion and/or therapeutic phlebotomy, and pregnancy and lactation. Each proband was also evaluated for viral hepatitis B and C and other hepatic disorders, excess ethanol intake, and hereditary, and acquired anemia. Iron overload was defined as evidence of systemic iron overload demonstrated by otherwise unexplained elevated serum ferritin concentration ($\geq$300 ng/mL in men, $\geq$200 ng/mL in women), increased hepatic iron content determined using hepatic biopsy specimens, or iron >4 g mobilized by phlebotomy. Complications of iron overload were evaluated and treated, and therapeutic phlebotomy was performed using standard methods. HFE mutation analysis for C282Y and H63D and human leukocyte antigen (HLA) immunophenotyping or molecular typing were performed using known methods. In some family members, HLA haplotyping had been performed previously for other disease associations, or their HLA type could be deduced from analysis of their kinship and HFE genotyping results. Measurement of serum iron and other clinical laboratory parameters and analysis of hepatic biopsy specimens were performed using routine methods. Control subjects (n=176) who were in apparently good health and were unrelated to the hemochromatosis probands were recruited from the general population. Iron parameters were measured and HLA typing was performed in two control subjects after HFE genotyping revealed that they had the S65C mutation.

EXAMPLE 2

HFE Gene Analysis

PCR amplification was used to detect mutations. Genomic DNA was prepared from peripheral blood buffy coat or saliva using the QIAmpBlood Kit (QIAGEN, Valencia, Calif.) or FTA Paper and FTA purification reagent (Fitzco Inc., Maple Plain, Minn.), respectively. Fragments were amplified from genomic DNA using eLONGase (Life Technologies, Gaithersburg, Md.) or HotStarTaq DNA polymerase (QIAGEN, Valencia, Calif.). Primers used to amplify each exon are shown in Table 3.

TABLE 4

| Human HFE genomic DNA |
|---|
| 1 ggatccttta accgaggaga ttattatagc cggagctctg aagcagcaat ctcagttctt |
| 61 gtgatagtga gcaaagaact acaaactaac accaaaatgc aagcttaaag caaagtttat |
| 121 tgaagcacaa taatacactc tgagggacag cgggcttatt tctgcgaagt gaactcagca |
| 181 cttctttaca gagctcaagg tgcttttatg gggtttgtgg ggaggagttg aggtttggc |
| 241 tgtatctgag tgacaggatg atgttatttg attgaagttt atagctatac aatctaaaat |
| 301 taaactgtgc atggtcttac ctataatttg ttaagaaaag cctcccaggg atgggggggc |
| 361 aaaactgtat gtaaattcta ttataatgat ggcatgatga acttggggtg aacttgaaga |
| 421 caggcttttg tgttgttggg catgtgccac cttagggaat ttccacctgt accctccttt |
| 481 ctctttctcc aggatatttt ggccacagac tttatcataa actccatccc ttagggtggc |
| 541 attagggtag tcttgggcct gaatttaggt gggccagtgg ctgtcttagt gacagccttt |
| 601 ccgctctctt ctgtcatccc ctcccaactg ctaatgtcta actacctaac aattacccat |
| 661 taaatcagtg tgtctggggt taggagcagg cctcaatatg tttaatcatt ctccagataa |
| 721 tcccaatact gtaaagtttg tgaaacactt gtcagataat tcaattatga aggctgtgga |

TABLE 4-continued

Human HFE genomic DNA

```
 781 acgtgtttca gtaggatcta attggttaat gttatgactt aattaatttg
     aatcaaaaaa 841 caaaatgaaa aagctttata tttctaagtc aaataagaca taagttggtc
     taaggttgag 901 ataaaatttt taaatgtatg attgaatttt gaaaatcata aatatttaaa
     tatctaaagt 961 tcagatcaga acattgcgaa gctactttcc ccaatcaaca acacccttc
     aggatttaaa 1021 aaccaagggg gacactggat cacctagtgt ttcacaagca ggtaccttct
     gctgaggag 1081 agagagaact aaagttctga aagacctgtt gcttttcacc aggaagtttt
     actgggcatc 1141 tcctgagcct aggcaatagc tgtagggtga cttctggagc catccccgtt
     tccccgcccc 1201 ccaaaagaag cggagattta acggggacgt gcggccagag ctggggaaat
     gggcccgcga 1261 gccaggccgg cgcttctcct cctgatgctt ttgcagaccg cggtcctgca
     ggggcgcttg 1321 ctgcgtgagt ccgagggctg cgggcgaact aggggcgcgg cggggtgga
     aaaatcgaaa 1381 ctagcttttt ctttgcgctt gggagtttgc taactttgga ggacctgctc
     aacccaatcc 1441 gcaagcccct ctccctactt tctgcgtcca daccccgtga gggagtgcct
     accactgaac 1501 tgcagatagg ggtccctcgc cccaggacct gccccctcc ccggctgtcc
     cggctctgcg 1561 gagtgacttt tggaaccgcc cactcccttc ccccaactag aatgctttta
     aataaatctc 1621 gtagttcctc acttgagctg agctaagcct ggggctcctt gaacctggaa
     ctcgggttta 1681 ttttccaatgt cagctgtgca gttttttccc cagtcatctc caaacaggaa
     gttcttccct 1741 gagtgcttgc cgagaaggct gagcaaaccc acagcaggat ccgcacgggg
     tttccacctc 1801 agaacgaatg cgttgggcgg tgggggcgcg aaagagtggc gttgggatc
     tgaattcttc 1861 accattccac ccacttttgg tgagacctgg ggtggaggtc tctagggtgg
     gaggctcctg 1921 agagaggcct acctcgggcc tttccccact cttggcaatt gttcttttgc
     ctggaaaatt 1981 aagtatatgt tagttttgaa cgtttgaact gaacaattct cttttcggct
     aggctttatt 2041 gatttgcaat gtgctgtgta attaagaggc ctctctacaa agtactgata
     atgaacatgt 2101 aagcaatgca ctcacttcta agttacattc atatctgatc ttatttgatt
     ttcactaggc 2161 atagggaggt aggagctaat aatacgttta ttttactaga agttaactgg
     aattcagatt 2221 atataactct tttcaggtta caaagaacat aaataatctg gttttctgat
     gttatttcaa 2281 gtactacagc tgcttctaat cttagttgac agtgattttg ccctgtagtg
```

TABLE 4-continued

Human HFE genomic DNA

```
      tagcacagtg
2341 ttctgtgggt cacacgccgg cctcagcaca gcactttgag ttttggtact
      acgtgtatcc
2401 acattttaca catgacaaga atgaggcatg gcacggcctg cttcctggca
      aatttattca
2461 atggtacacg gggctttggt ggcagagctc atgtctccac ttcatagcta
      tgattcttaa
2521 acatcacact gcattagagg ttgaataata aaatttcatg ttgagcagaa
      atattcattg
2581 tttacaagtg taaatgagtc ccagccatgt gttgcactgt tcaagcccca
      agggagagag
2641 cagggaaaca agtctttacc cttgatatt ttgcattcta gtgggagaga
      tgacaataag
2701 caaatgagca gaaagatata caacatcagg aaatcatggg tgttgtgaga
      agcagagaag
2761 tcagggcaag tcactctggg gctgacactt gagcagagac atgaaggaaa
      taagaatgat
2821 attgactggg agcagtattt cccaggcaaa ctgagtgggc ctggcaagtt
      ggattaaaaa
2881 gcgggttttc tcagcactac tcatgtgtgt gtgtgtgggg ggggggcgg
      cgtgggggtg
2941 ggaagggga ctaccatctg catgtaggat gtctagcagt atcctgtcct
      ccctactcac
3001 taggtgctag gagcactccc ccagtcttga caaccaaaaa tgtctctaaa
      ctttgccaca
3061 tgtcacctag tagacaaact cctggttaag aagctcgggt tgaaaaaaat
      aaacaagtag
3121 tgctggggag tagaggccaa gaagtaggta atgggctcag aagaggagcc
      acaaacaagg
3181 ttgtgcaggc gcctgtaggc tgtggtgtga attctagcca aggagtaaca
      gtgatctgtc
3241 acaggctttt aaaagattgc tctggctgct atgtggaaag cagaatgaag
      ggagcaacag
3301 taaaagcagg gagcccagcc aggaagctgt tacacagtcc aggcaagagg
      tagtggagtg
3361 ggctgggtgg gaacagaaaa gggagtgaca aaccattgtc tcctgaatat
      attctgaagg
3421 aagttgctga aggattctat gttgtgtgag agaaagagaa gaattggctg
      ggtgtagtag
3481 ctcatgccaa ggaggaggcc aaggagagca gattcctgag ctcaggagtt
      caagaccagc
3541 ctgggcaaca cagcaaaacc ccttctctac aaaaaataca aaaattagct
      gggtgtggtg
3601 gcatgcacct gtgatcctag ctactcggga ggctgaggtg gagggtattg
      cttgagccca
3661 ggaagttgag gctgcagtga gccatgactg tgccactgta cttcagccta
      ggtgacagag
3721 caagaccctg tctcccctga cccctgaaa aagagaagag ttaaagttga
      ctttgttctt
3781 tattttaatt ttattggcct gagcagtggg gtaattggca atgccatttc
      tgagatggtg
```

TABLE 4-continued

Human HFE genomic DNA

```
3841 aaggcagagg aaaqagcagt ttggggtaaa tcaaggatct gcatttggac
     atgttaagtt 3901 tgagattcca gtcaggcttc caagtggtga ggccacatag gcagttcagt
     gtaagaattc 3961 aggaccaagg cagggcacgg tggctcactt ctgtaatccc agcactttgg
     tggctgaggc 4021 aggtagatca tttgaggtca ggagtttgag acaagcttgg ccaacatggt
     gaaaccccat 4081 gtctactaaa aatacaaaaa ttagcctggt gtggtggcgc acgcctatag
     tcccaggttt 4141 tcaggaggct taggtaggag aatcccttga acccaggagg tgcaggttgc
     agtgagctga 4201 gattgtgcca ctgcactcca gcctgggtga tagagtgaga ctctgtctca
     aaaaaaaaaa 4261 aaaaaaaaaa aaaaaaaaaa aactgaagga attattcctc aggatttggg
     tctaatttgc 4321 cctgagcacc aactcctgag ttcaactacc atggctagac acaccttaac
     attttctaga 4381 atccaccagc tttagtggag tctgtctaat catgagtatt ggaataggat
     ctgggggcag 4441 tgagggggtg gcagccacgt gtggcagaga aaagcacaca aggaaagagc
     acccaggact 4501 gtcatatgga agaaagacag gactgcaact caccccttcac aaaatgagga
     ccagacacag 4561 ctgatggtat gagttgatgc aggtgtgtgg agcctcaaca tcctgctccc
     ctcctactac 4621 acatggttaa ggcctgttgc tctgtctcca ggttcacact ctctgcacta
     cctcttcatg 4681 ggtgcctcag agcaggacct tggtcttttcc ttqtttgaag ctttgggcta
     cgtggagac 4741 cagctgttcg tgttctatga tcatgagagt cgccgtgtgg agccccgaac
     ccatgggtt 4801 tccagtagaa tttcaagcca gatgtggctg cagctgagtc agagtctgaa
     agggtgggat 4861 cacatgttca ctgttgactt ctggactatt atggaaaatc acaaccacag
     caagggtatg 4921 tggagagggg gcctcaccct cctgaggttg tcagagcttt tcatcttttc
     gaatttgctt 4981 aaggaaacag ctggaagtct gaggtcttgt gggagcaggg aagagggaag
     gaatttgctt 5041 cctgagatca tttggtcctt ggggatggtg gaaataqgga cctattcctt
     tggttqcaqt 5101 taacaaggat gggggatttttt ccagagtcca acaccctgca ggtcatactg
     ggctgtgaaa 5161 tgcaagaaga caacagtacc gagggctact ggaagtacgg gtatgatggg
     caggaccacc 5221 ttgaattctg ccctgacaca ctggattgga gagcagcaga acccagggcc
     tggcccacca 5281 agctggagtg ggaaaggcac aagattcggg ccaggcagaa cagggcctac
     ctggagaggg 5341 aatgccctgc acagctgcag cagttgctgg agctggggag aggtgttttg
     gaccaacaag
```

TABLE 4-continued

Human HFE genomic DNA

```
5401 gtatggtgga aacacacttc tgcccctata ctctagtggc agagtggagg
     aggttgcagg 5461 gaacggaatc cctggttgga gtttcagagg tggctgaggc tgtgtgcctc
     tccaaattct 5521 gggaagggac tttctcaatc ctagagtctc taccttataa ttgagatgta
     tgagacagac 5581 acaagtcatg ggtttaattt cttttctcca tgcatatggc tcaaagggaa
     gtgtctatgg 5641 cccttgcttt ttatttaacc ataatctttt tgtatattta tacctgttaa
     aaattcagaa 5701 atgtcaaggc cgggaacggt ggatcacccc tgtaatccca gcactttggg
     aggccgaggc 5761 gggtggtcac aaggtcagga gtttgagacc agcctgacca acatggtgaa
     acccgtctat 5821 aaaaaaatac aaaaattaga tggtcacagt catgcgcacc tgtagtccaa
     gctaattgga 5881 aggctgaggc aggagcatcg cttgaacctg ggaagcggaa gttgcactga
     gccaagatcg 5941 cgccactgca ctccagccta ggcagcagag tgagactcca tcttaaaaaa
     aaaaaaaaaa 6001 aaaagagaa ttcagagatc tcagctatca tatgaatacc aggacaaaat
     atcaagtgag 6061 gccacttatc agagtagaag aatcctttag gttaaaagtt tctttcatag
     aacatagcaa 6121 taataactga agctacctat cttacaagtc cgcttcttat aacaatgcct
     cctaggttga 6181 accaggtgaa actgaccatc tgtattcaat cattttcaat gcacataaag
     ggcaatttta 6241 tctatcagaa caaagaacat gggtaacaga tatgtatatt tacatgtgag
     gagaacaagc 6301 tgatctgact gctctccaag tgacactgtg ttagagtcca atcttaggac
     acaaaatggt 6361 gtatctcctg tagcttgttt ttttctgaaa agggtatttc cttcctccaa
     cctatagaag 6421 gaagtgaaag ttccagtctt cctggcaagg gtaaacagat cccctctcct
     catccttcct 6481 ctttcctgtc aagtgcctcc tttggtgaag gtgacacatc atgtgacctc
     ttcagtgacc 6541 actctacggt gtcgggcctt gaactactac ccccagaaca tcacaatgaa
     gtggctgaag 6601 gataagcagc caatggatgc caaggagttc gaacctaaag acgtattgcc
     caatggggat 6661 gggacctacc agggctggat aaccttggct gtaccccctg gggagagca
     gagatatacg 6721 tgccaggtgg agcacccagg cctggatca cccctcattg tgatctgggg
     tatgtgactg 6781 atgagagcca ggagctgaga aaatctattg ggggttgaga ggagtgcctg
     aggaggtaat 6841 tatggcagtg agatgaggat ctgctctttg ttaggggatg ggctgagggt
     ggcaatcaaa 6901 ggctttaact tgctttttct gttttagagc cctcaccgtc tggcacccta
```

TABLE 4-continued

Human HFE genomic DNA

```
      gtcattggag 6961  tcatcagtgg aattgctgtt tttgtcgtca tcttgttcat tggaattttg
      ttcataatat 7021  taaggaagag gcaggttca agtgagtagg aacaaggggg aagtctatta
      gtacctctgc 7081  cccagggcac agtgggaaga ggggcagagg ggatctggca tccatgggaa
      gcattttct 7141  catttatatt ctttggggac accagaagct ccctgggaga cagaaaataa
      tggttctcca 7201  cagaatgaaa gtctctaatt caacaaacat cttcagagca cctactattt
      tgcaagagct 7261  gtttaaggta gtacaggggc tttgaggttg agaagtcact gtggctattc
      tcagaaccca 7321  aatctggtag ggaatgaaat tgatagcaag taaatgtag taaagaagac
      cccatgaggt 7381  cctaaagcag gcaggaagca aatgcttagg gtgtcaaagg aaagaatgat
      cacattcagc 7441  tggggatcaa gatagccttc tggatcttga aggagaagct ggattccatt
      aggtgaggtt 7501  gaagatgatg ggaggtctac acagacggag caaccatgcc aagtaggaga
      gtataaggca 7561  tactgggaga ttagaaataa ttactgtacc ttaaccctga gtttgcttag
      ctatcactca 7621  ccaattatgc atttctaccc cctgaacata tgtggtgtag ggaaaagaga
      atcagaaaga 7681  agccagctca tacagagtcc aagggtcttt tgggatattg ggttatgatc
      actggggtgt 7741  cattgaagga tcctaagaaa ggaggaccac gatctcccac atatggtgaa
      tgtgttgtta 7801  agaagttaga tgagaggtga ggagaccagt tagaaagcca ataagcattt
      ccagatgaga 7861  gataatggtt cttgaaatcc aatagtgccc aggtctaaat tgagatgggt
      gaatgaggaa 7921  aataaggaag agagaagagg caagatggtg cctaggtttg tgatgcctct
      ttcctgggtc 7981  tcttgtctcc acaggaggag ccatggggca ctacgtctta gctgaacgtg
      agtgacacgc 8041  agcctgcaga ctcactgtgg gaaggagaca aaactagaga ctcaaagagg
      gagtgcattt 8101  atgagctctt catgtttcag gagagagtgg aacctaaaca tagaaattgc
      ctgacgaact 8161  ccttgatttt agccttctct gttcatttcc tcaaaaagat ttccccattt
      aggtttctga 8221  gttcctgcat gccggtgatc cctagctgtg acctctcccc tggaactgtc
      tctcatgaac 8281  ctcaagctgc atctagaggc ttccttcatt tcctccgtca cctcagagac
      atacacctat 8341  gtcatttcat ttcctatttt tggaagagga ctccttaaat ttgggggact
      tacatgattc 8401  attttaacat atgagaaaag cttttgaaccc tgggacgtgg ctagtcataa
      ccttaccaga
```

TABLE 4-continued

Human HFE genomic DNA 8461 tttttacaca tgtatctatg cattttctgg acccgttcaa cttttccttt
     gaatcctctc 8521 tctgtgttac ccagtaactc atctgtcacc aagccttggg gattcttcca
     tctgattgtg 8581 atcgtgagttg cacgctatg aaggctgtac actgcacgaa tggaagaggc
     acctgtccca 8641 gaaaaagcat catggctatc tgtgggtagt atgatgggtg tttttagcag
     gtaggaggca 8701 aatatcttga aagggttgt gaagaggtgt tttttctaat tggcatgaag
     gtgtcataca 8761 gatttgcaaa gtttaatggt gccttcattt gggatgctac tctagtattc
     cagacctgaa 8821 gaatcacaat aattttctac ctggtctctc cttgttctga taatgaaaat
     tatgataagg 8881 atgataaaag cacttacttc gtgtccgact cttctgagca cctacttaca
     tgcattactg 8941 catgcacttc ttacaataat tctatgagat aggtactatt atccccattt
     ctttttaaa 9001 tgaagaaagt gaagtaggcc gggcacggtg gctcacgcct gtaatcccag
     cactttggga 9061 ggccaaagc ggtggatcac gaggtcagga gatcgagacc atcctggcta
     acatggtgaa 9121 accccatctc taataaaaat acaaaaaatt agctgggcgt ggtggcagac
     gcctgtagtc 9181 ccagctactc ggaaggctga ggcaggagaa tggcatgaac ccaggaggca
     gagcttgcag 9241 tgagccgagt ttgcgccact gcactccagc ctaggtgaca gagtgagact
     ccatctcaaa 9301 aaaataaaaa taaaaataaa aaatgaaaa aaaaagaaa gtgaagtata
     gagtatctca 9361 tagtttgtca gtgatagaaa caggtttcaa actaagtaaa tctgaccgtt
     tgatacatct 9421 cagacaccac tacattcagt agtttagatg cctagaataa atagagaagg
     aaggagatgg 9481 ctcttctctt gtctcattgt gtttcttctg aatgagcttg aatcacatga
     agggggaacag 9541 cagaaaacaa ccaactgatc ctcagctgtc atgtttcctt taaaagtccc
     tgaaggaagg 9601 tcctggaatg tgactcccttt gctcctctgt tgctctcttt ggcattcatt
     tctttggacc 9661 ctacgcaagg actgtaattg gtggggacag ctagtggccc tgctgggctt
     cacacacggt 9721 gtcctcccta ggccagtgcc tctggagtca gaactctggt ggtatttccc
     tcaatgaagt 9781 ggagtaagct ctctcatttt gagatggtat aatggaagcc accaagtggc
     ttagaggatg 9841 cccagtcct tccatggagc cactgggtt ccggtgcaca ttaaaaaaaa
     aatctaacca 9901 ggacattcag gaattgctag attctgggaa atcagttcac catgttcaaa
     agagtctttt 9961 tttttttttt gagactctat tgcccaggct ggagtgcaat ggcatgatct
     cggctcactg

TABLE 4-continued

Human HFE genomic DNA

```
10021  taacctctgc ctcccaggtt caagcgattc tcctgtctca gcctcccaag
       tagctgggat 10081  tacaggcgtg caccaccatg cccggctaat tttgtatttt ttagtagaga
       cagggtttca 10141  ccatgttggc caggctggtc tcgaactctc ctgacctcgt gatccgcctg
       cctcggcctc 10201  ccaaagtgct gagattacag gtgtgagcca ccctgcccag ccgtcaaaag
       agtcttaata 10261  tatatatcca gatggcatgt gtttacttta tgttactaca tgcacttggc
       tgcataaatg 10321  tggtacaagc attctgtctt gaagggcagg tgcttcagga taccatatac
       agctcagaag 10381  tttcttcttt aggcattaaa ttttagcaaa gatatctcat ctcttctttt
       aaaccatttt 10441  cttttttgt ggttagaaaa gttatgtaga aaaagtaaa tgtgatttac
       gctcattgta 10501  gaaaagctat aaaatgaata caattaaagc tgttatttaa ttagccagtg
       aaaaactatt 10561  aacaacttgt ctattacctg ttagtattat tgttgcatta aaaatgcata
       tactttaata 10621  aatgtacatt gtattgtata ctgcatgatt ttattgaagt tcttgttcat
       cttgtgtata 10681  tacttaatcg ctttgtcatt ttggagacat ttattttgct tctaatttct
       ttacattttg 10741  tcttacggaa tattttcatt caactgtggt agccgaatta atcgtgtttc
       ttcactctag 10801  ggacattgtc gtctaagttg taagacattg gttattttac cagcaaacca
       ttctgaaagc 10861  atatgacaaa ttatttctct cttaatatct tactatactg aaagcagact
       gctataaggc 10921  ttcacttact cttctacctc ataaggaata tgttacaatt aatttattag
       gtaagcattt 10981  gtttatatt ggttttattt cacctgggct gagatttcaa gaaacacccc
       agtcttcaca 11041  gtaacacatt tcactaacac atttactaaa catcagcaac tgtggcctgt
       taattttttt 11101  aatagaaatt ttaagtcctc attttctttc ggtgtttttt aagcttaatt
       tttctggctt 11161  tattcataaa ttcttaaggt caactacatt tgaaaaatca aagacctgca
       ttttaaattc 11221  ttattcacct ctggcaaaac cattcacaaa ccatggtagt aaagagaagg
       gtgacacctg 11281  gtggccatag gtaaatgtac cacggtggtc cggtgaccag agatgcagcg
       ctgagggttt 11341  tcctgaaggt aaaggaataa agaatgggtg gaggggcgtg cactggaaat
       cacttgtaga 11401  gaaaagcccc tgaaatttg agaaaacaaa caagaaacta cttaccagct
       atttgaattg 11461  ctggaatcac aggccattgc tgagctgcct gaactgggaa cacaacagaa
       ggaaaacaaa 11521  ccactctgat aatcattgag tcaagtacag caggtgattg aggactgctg
```

TABLE 4-continued

Human HFE genomic DNA

```
       agaggtacag
11581  gccaaaattc ttatgttgta ttataataat gtcatcttat aatactgtca
       gtattttata
11641  aaacattctt cacaaactca cacacattta aaaacaaaac actgtctcta
       aaatccccaa
11701  atttttcata aactcagttt taaactaact tttttcaaa ccacaatctg
       atttaacaat
11761  gactatcatt taaatatttc tgactttcaa attaaagatt ttcacatgca
       ggctgatatt
11821  tgtaattgtg attctctctg taggctttgg gtataatgtg ttcttttcct
       tttttgcatc
11881  agcgattaac ttctacactc taacatgtag aatgttacta caatattaaa
       gtattttgta
11941  tgacaatttt atttgaaagc ctaggatgcg ttgacatcct gcatgcattt
       attacttgat
12001  atgcatgcat tctggtatct caagcattct atttctgagt aattgtttaa
       ggtgtagaag
12061  agatagatat ggtggatttg gagttgatac ttatatattt tctatttctt
       ggatggatga
12121  atttgtacat taaaagtttt ccatgg
```

(SEQ ID NO:27; GENBANK® Accession No. Z92910)

Exon 1 spans nt 1028–1324, inclusive; exon 2 spans nt 4652–4915, inclusive; exon 3 spans nt 5125–5400, inclusive; exon 4 spans nt 6494–6769, inclusive; exon 5 spans nt 6928–7041, inclusive; exon 6 spans nt 7995–9050, inclusive, and exon 7 spans nt 10206–10637, inclusive. Intron 4 spans nt 6770–6927, inclusive, and intron 5 spans nt 7042–7994, inclusive.

Total RNA for the RT-PCR was prepared from 1.5 mL of whole blood using the RNeasy Blood Kit (QIAGEN, Valencia, Calif.). Total messenger RNA encoding the HFE gene was transcribed and amplified with the primers shown above using standard methods, e.g., the Superscript ONE-STEP RT- PCR System (Life Technologies, Gaithersburg, Md.). The amplified product was directly subcloned into the pCR2.1-TOPO vector and transfected into TOP 10 bacteria (Invitrogen, Carlsbad, Calif.). Plasmid DNAs isolated from the subcloning were prepared with the UltraClean Mini Prep Kit (Mo Bio, Solana Beach, Calif.) and sequenced.

DNA sequencing was performed using the ABI Prism BigDye Terminator Cycle Sequencing Ready Reaction Kit (PE Applied Biosystems, Foster City, Calif.) and analyzed on an ABI Prism 377.

To detect mutations in exon 2 of the HFE gene, the genomic DNA of probands and normal control subjects were amplified and subjected to a dot blot hybridization assay. 1.0 µl of each resulting PCR product was then applied to a Magna Graph nylon membrane (MSI, Westboro, Mass.). The membranes were treated with 0.5 N NaOH/1.5 M NaCl to denature the DNA, neutralized with 0.5 M Tris-HCl (pH 8.0)/1.5 M NaCl, and rinsed with 2×SSC (1×SSC=0.15 M NaCl/0.015 M sodium citrate, pH 7.0). The DNAs were fixed on the membrane by UV irradiation using a Stratalinker 1800 (Stratagene, Inc., La Jolla, Calif.). The ECL 3'-oligolabelling and detection system (Amersham, Arlington Heights, Ill.) was used for synthesis of labeled oligonucleotide probes, hybridization, and signal detection.

The oligonucleotide sequences used to detect each point mutation were (substituted bases are shown as upper case letters):

TABLE 5

Oligonucleotide Probes

| Point Mutation | Oligonucleotide |
|---|---|
| G93R mutation | gtctgaaaCggtgggat (SEQ ID NO:28) |
| I105T mutation | acttctggactaCtatgg (SEQ ID NO:29) |
| S65C mutation | atcatgagTgtcgccgt (SEQ ID NO:30) |

For signal detection, each oligonucleotide was labeled with fluorescein-11-dUTP using terminal deoxynucleotidyl transferase according to the manufacturer's instructions (Amersham Ltd., Arlington Heights, Ill.). The membranes were prehybridized in 5×SSC, 0. 1% Hybridization buffer component, 0.02% SDS, 5% LiquidBlock at 42° C. for approximately 2 hours. Labelled oligonucleotide probes were added to individual bags containing the membranes and prehybridization buffer and incubated at 42° C. overnight. The blots were washed twice with 5×SSC, 0.1% SDS for 5 minutes at room temperature. Stringency washes for hybridization with oligonucleotides having the sequence of SEQ ID NO:30 or 28 were performed twice in 0.2×SSC/ 0.1% SDS for 15 minutes at 42° C. Membranes probed with an oligonucleotide having the sequence of SEQ ID NO:29 was washed twice under less stringent conditions (0.5×SSC/ 0.1% SDS, 15 minutes at 42° C.). Detection of a fluorescent signal was performed according to standard methods.

EXAMPLE 3

Characterization of Probands

The mean age of the twenty probands was 44±11 years (range 27–62 years); thirteen (65.0%) were men and seven (35.0%) were women. Eleven had iron overload. One had hepatic cirrhosis, two had diabetes mellitus, four had arthropathy, and two had hypogonadotrophic hypogonadism. One proband also had hereditary stomatocytosis, another had beta-thalassemia trait, a third had ethanol intake >60 g daily, and a fourth had porphyria cutanea tarda. No proband had evidence of excess oral or parenteral iron intake, or of viral hepatitis B or C. At diagnosis of hemochromatosis, evaluation for common HFE mutations revealed that eleven probands were C282Y heterozygotes, five were H63D heterozygotes, and four did not inherit C282Y or H63D.

The mean age of the initial 176 control subjects was 52±15 years (range 18–86 years); 79 (44.9%) were men and 97 (55.1%) were women. There was no significant difference in the mean ages of men and women. Frequencies of HFE genotypes among the control subjects are shown in Table 6. These values are similar to those previously reported from normal persons from the same geographic area.

TABLE 6

Frequencies of HFE Genotypes in Alabama Subjects.

| HFE Genotype | Hemochromatosis Probands with "Atypical" HFE Genotypes, % (n) | Normal Control Subjects, % (n) |
|---|---|---|
| wt/wt | 15.00 (3) | 60.23 106) |
| C282Y/wt | 45.00 (9) | 13.06 (23) |
| H63D/wt | 20.00 (4) | 15.34 (27) |
| S65C/wt | 5.00 (1) | 1.14 (2) |
| C282Y/S65C | 5.00 (1) | 0 |
| C282Y/G93R | 5.00 (1) | 0 |
| H63D/I105T | 5.00 (1) | 0 |
| H63D/C282Y | 0 | 6.82 (12) |
| H63D/H63D | 0 | 3.41 (6) |

Results are expressed as percentage (n). The wild-type (wt) allele was defined as the HFE configuration in which the mutations C282Y, H63D, S65C, I105T, or G93R were not detected.

EXAMPLE 4

Identification of Novel HFE Mutations in Hemochromatosis Probands

Figure 2:
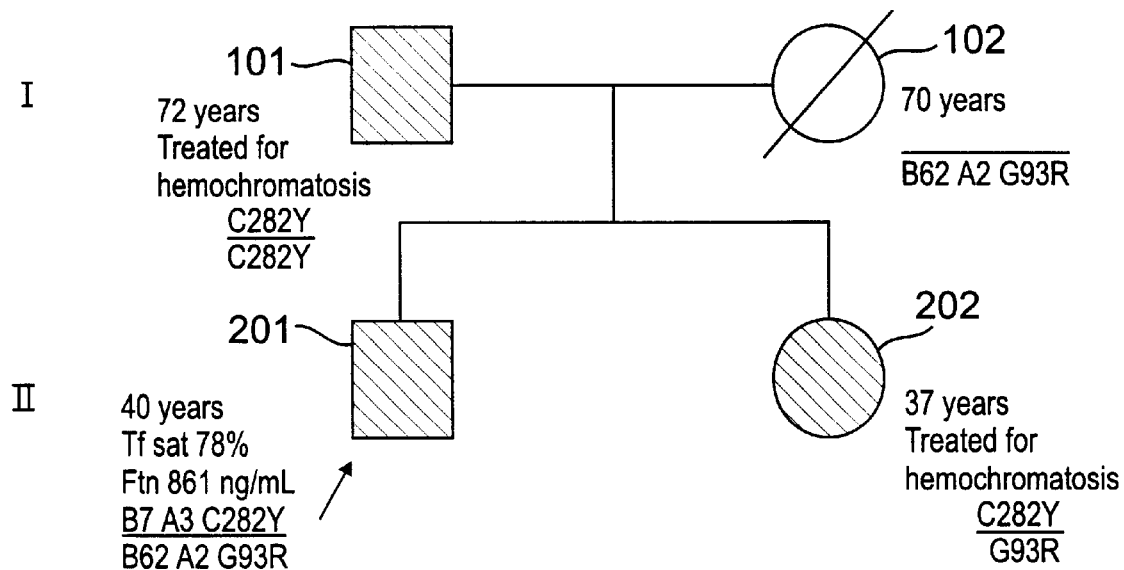
FIG. 2 is a diagram of the family of proband 2 (HFE genotype C282Y/G93R). Symbols and abbreviations are the same as those described for FIG. 1. Proband 2 is indicated with an arrow. G93R, C282Y, and wt alleles are known to exist only on separate chromosomes. The father and sister of the proband are being treated for hemochromatosis.

The following novel mutations (missense mutations) were identified in probands 1 and 2: exon 2, nt 314T→C (I105T), and exon 2, nt 277G→C (G93R), respectively (Table 7; FIGS. 1 and 2). Probands 3 and 4 had a S65C mutation The S65C mutation has been observed in hemochromatosis patients but has not been deemed to be indicative of a disease state. In contrast, the data presented herein indicate that the S65C mutation is diagnostic of a disease state. This result is surprising in view of earlier observations. Other than C282Y or H63D, no HFE exon mutations were detected in the remaining sixteen of the twenty probands (Table 6). Nine probands were heterozygous for a base-pair change at intron 2, nt 4919T/C (SEQ ID NO:27); two probands were homozygous for this base-pair change. Heterozygosity for a base-pair change in intron 4 (nt 6884T→C) was detected only in probands 3 and 4, both of whom also inherited S65C. One proband was heterozygous for a base-pair change at intron 5, nt 7055A→G.

Using dot blot methodology, heterozygosity for the S65C mutation was detected in two of 176 normal control subjects (Table 6). The G93R or I105T mutations were not detected in normal control subjects (Tables 6 and 8).

EXAMPLE 5

Association of Novel HFE Coding Region Mutations to C282Y and H63D and HFE Intron Alleles In proband 1, two mutations of exon 2 (H63D and I105T) were detected. After subcloning the genomic fragment, the subclones revealed that these mutations occurred on separate chromosomes; this observation was confirmed by family studies indicating segregation of I105T

TABLE 7

Phenotypes and Uncomnon HFE Genotypes in Alabama Subjects*

| Subject† | Age (years), Sex | HFE Genotype | HLA Type | Transferrin Saturation, % | Serum Ferritin, ng/mL | Hepatocyte Iron Grade | Phlebotomy, Units |
|---|---|---|---|---|---|---|---|
| Proband 1 | 52 M | H63D/I105T | A2, 3; B7, 7 | 62 | 868 | 2+ | 20 |
| Proband 2‡ | 40 M | C282Y/G93R | A2, 3; B7, 62 | 78 | 861 | 4+ | 34 |
| Proband 3§ | 47 F | C282Y/S65C | A2, 32; B8, 44; Bw4, 6; Cw5, 7 | 90 | 281 | 3+ | 37 |
| Proband 4** | 81 F | S65C/wt | A2, 32; B14, 62 | 100 | 5,135 | N.D. | 37 |
| Normal Control 1 | 28 M | S65C/wt | A2, 31; B35, 60 | 28 | 141 | N.D. | N.D. |
| Normal Control 2 | 69 M | S65C/wt | A24, 26; B8, B37; Bw4, 6; Cw6, 5 (or 7) | 42 | 747 | 2+ | N.D. |

*Serum transferrin saturation, serum ferritin concentration, and percutaneous hepatic biopsy were performed before therapeutic phlebotomy was initiated. Reference ranges for these parameters are 15–45%; 20–300 ng/nL (men) and 20–200 ng/mL (women); and 0 −1+, respectively. Iron depletion (serum ferritin ≦ 20 ng/mL) was induced by removing the indicated numbers of units of blood. None of these persons had evidence of hepatic cirrhosis, diabetes mellitus, hemochromatosis-associatedarthropathy, hypogonadotrophic hypogonadism, other endocrinopathy, or cardiomopathy. N.D. = not done. The mutations indicated are exon 4, nt 845G→A (C282Y); exon 2, nt 187C → G (H63D); exon 2, nt 314T → C (I105T); exon 2, nt 277G → C (G93R); and exon 2, nt 193A → T (S65C). The wild-type (wt) allele was defined as an HFE allele in which the mutations C282Y, H63D, S65C, I105T, or G93R were not detected.
†Countries of origin: Probands 1 and 2, England; Proband 3, Wales, England, and Americas (Cherokee); Proband 4, England and Ireland; Normal Control 1, England; Normal Control 2, The Netherlands.
‡The father and sister of Proband 2 are presently undergoing therapy for hemochromatosis and iron overload, but their clinical and genetic data were unavailable.
§Proband 3 had porphyria cutanea tarda alleviated with therapeutic phlebotomy.

TABLE 7-continued

Phenotypes and Uncomnon HFE Genotypes in Alabama Subjects*

| Subject† | Age (years), Sex | HFE Genotype | HLA Type | Transferrin Saturation, % | Serum Ferritin, ng/mL | Hepatocyte Iron Grade | Phlebotomy, Units |
|---|---|---|---|---|---|---|---|

**Proband 4 had hereditary stomatocytosis unaffected by phlebotomy treatments. 37 units of blood were removed by phlebotomy before treatment was discontinued due to stroke apparently unrelated to anemia or iron overload (post-treatrnent serum ferritin 1,561 ng/mL). Her 59 year-old daughter (who does not have hereditary stomatocytosis) had transferrin saturation 42%, serum ferritin 62 ng/mL, HLA type A1, 32; B14, 15; Bw4, 6; Cw3, 8, and HFE genotype S65C/63D. These data permitted assignment of theS65C mutation in this family to a haplotype carrying HLA-A32; linkage of S65C and HLA-A32 was also observed in the family of Proband 3.

TABLE 8

Frequencies of HFE Alleles in Alabama Subjects.

|  | wt* | C282Y | H63D | S65C† | I105T | G93R |
|---|---|---|---|---|---|---|
| Hemochromatosis Probands with "Atypical" HFE Genotypes (n = 20) | 0.500 | 0.275 | 0.125 | 0.050 | 0.025 | 0.025 |
| Normal Control Subjects (n = 176) | 0.750 | 0.099 | 0.145 | 0.006 | ‡ | ‡ |

The wild-type (wt) allele was defined as an HFE allele in which the mutations C282Y, H63D, S65C, I105T, or G93R were not detected.
†S65C was detected in 2 of 22 (0.091) proband chromosomes and in 2 of 266 (0.0075) control chromosomes that did not bear the C282Y, H63D, S65C, I105T, or G93R mutation.
‡Based on this data set, the frequency of the I105T and G93R HFE alleles is estimated to be <0.0028, respectively.

and H63D (FIG. 1). In proband 2 (HFE genotype C282Y/G93R), RT-PCR analysis (with subsequent subcloning and sequencing) revealed that these HFE mutations occurred on separate chromosomes. Family studies of proband 3 (HFE genotype C282Y/S65C) indicated that the C282Y and S65C HFE alleles segregated independently, establishing their occurrence on separate chromosomes (Table 7, FIG. 3).

In proband 1 (HFE genotype H63D/I105T), the I105T mutation was co-inherited with HLA-A3, B7. In probands 3 and 4 and their respective families, S65C was inherited on the same chromosome as HLA-A32, indicating that HLA-A32 is a marker for chromosomes bearing the S65C mutation, and individuals with HLA-A32 have an increased risk for developing hemochromatosis. The G93R mutation is associated with HLA-A2, and individuals with that haplotype have an increased risk for developing hemochromatosis. The I105T mutation is associated with HLA-A3, e.g., HLA-A3, B7, and individuals with that haplotype have an increased risk for developing hemochromatosis. Among twenty probands tested, the nucleotide polymorphism in intron 4 (nt 6884T→C) was detected in probands 3 and 4, both of whom also had S65C. Subjects that tested positive for the S65C mutation all were found to have the intron 4 (6884T→C) mutation, including two probands (3 and 4), their families, and two normal controls.

EXAMPLE 6

HFE Coding Region Mutations and Clinical Phenotype

Figure 3:
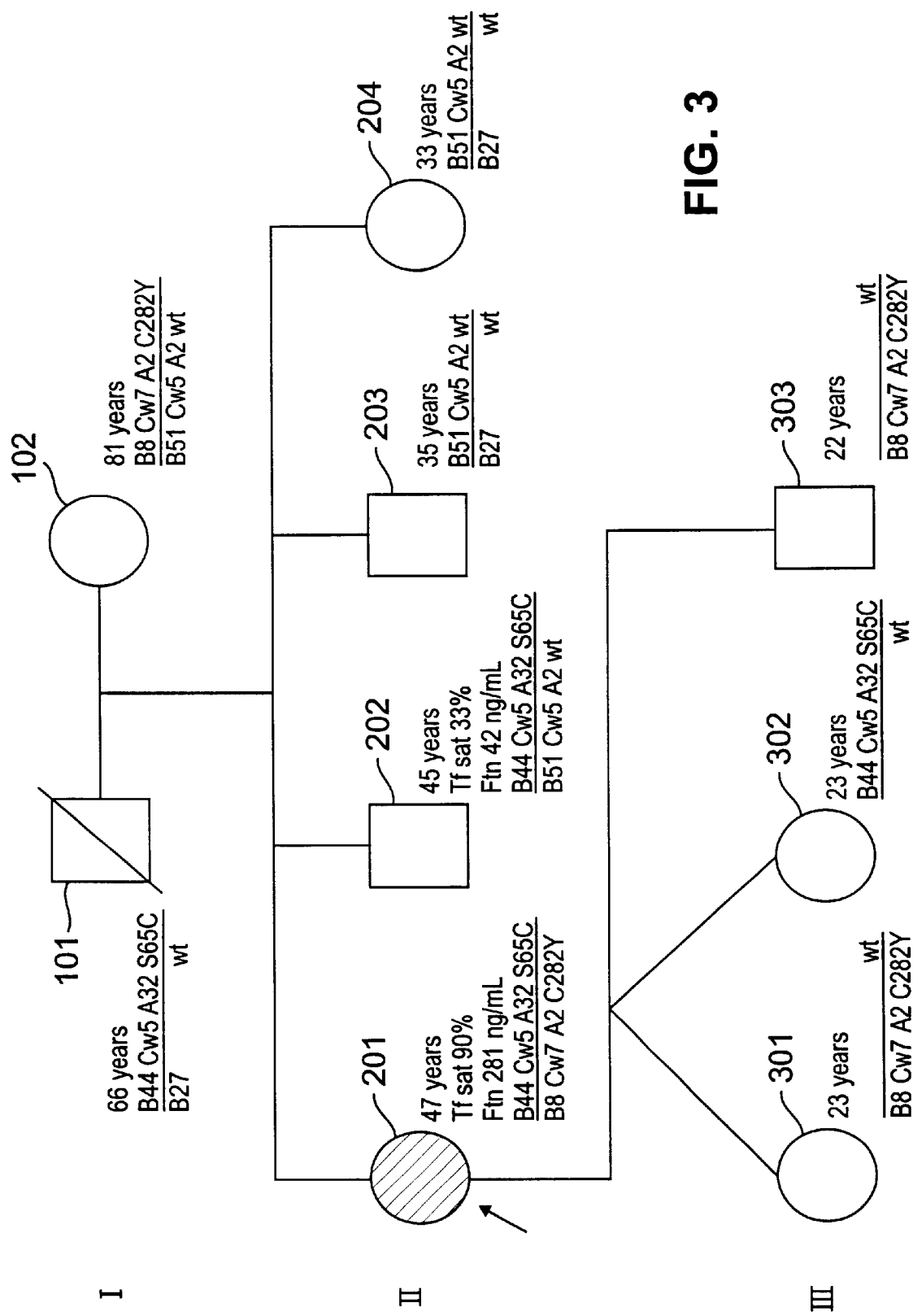
FIG. 3 is a diagram of the family of proband 3 (HFE genotype C282Y/S65C). Symbols and abbreviations are the same as those described for FIG. 1. Proband 3 is indicated with an arrow. S65C, C282Y, and wt alleles are know to exist only on separate chromosomes. Proband 3 also has porphyria cutanea tarda, and her brother (II, 203 ) has ankylosing spondylitis.

The I105T and G93R mutations were associated with a hemochromatosis clinical phenotype in probands 1 and 2 who also inherited H63D and C282Y, respectively. Proband 3 had clinical evidence of hemochromatosis, iron overload, and porphyria cutanea tarda associated with compound heterozygosity for C282Y and S65C. Proband 4 had severe iron overload associated with heterozygosity for S65C and co-inheritance of hereditary stomatocytosis (Table 7). The sister of proband (HFE genotype I105T/wt) was not completely evaluated for hyperferritinemia (FIG. 1). Otherwise, family members of probands who were heterozygous for novel HFE mutations described herein had little or no evidence of abnormal iron parameters, a hemochromatosis phenotype, or of iron overload (Table 7 and 9; FIGS. 1 and 3). Normal Control 1 who had HFE genotype S65C/wt had a

TABLE 9

Hemochromatiosis (HC) Family study/patent

| Subject/Age/Sex | HLA Type | exon 2 | exon 4 | intron 4 5636bp | Tf sat** % | Ftn** ng/ml | Diagnosis/Hepatocyte Iron grade |
|---|---|---|---|---|---|---|---|
| Proband 1/57M (201) | A2, 3; B7, 7 | H63D/H, 1105T/1 | Wt | T | 62 | 868 | HC/2+ |
| brother/45M (204) |  | H63D/H | Wt | T* | 31 | 186 |  |
| sister/50F (203) | A3, 3; B7, 7 | 1105T | Wt* | T* | 37 | 576 |  |
| daughter/31F (301) | A32, 68; B7, 44 | 1105T/1 | Wt* | T* | 31 | 56 |  |
| son/27M (302) | A2, 68; B7, 44 | H63D/H | Wt* | T* | 33 | 44 |  |
| Proband 2/40M | A2, 3; B7, 62 | G93R/G | C282Y/C | T | 78 | 861 | HC/4+ |
| Father |  | Wt | C282Y/Y* | T* |  |  | HC |
| Sister |  | G93R/G | C282Y/C* | T* |  |  | HC |
| Proband 3/47 (201) | A2, 32; B8, 44 | S65C/S | C282Y/C | T/C | 90 | 281 | HC/3+ |

TABLE 9-continued

Hemochromatosis (HC) Family study/patent

| Subject/Age/Sex | HLA Type | exon 2 | exon 4 | intron 4 5636bp | Tf sat** % | Ftn** ng/ml | Diagnosis/Hepatocyte Iron grade |
|---|---|---|---|---|---|---|---|
| brother/45M (202) | A2, 32; B44, 51 | S65C/S | Wt | T/C | 33 | 42 | |
| nother/81F (102) | A2, 2; B8, 51 | Wt | C282Y/C | T* | NT | NT | |
| sister/33F (204) | A2, 7; B27, 51 | Wt | Wt | T* | NT | NT | |
| brother/35M (203) | A2, 7; B27, 51 | Wt | Wt* | T* | NT | NT | |
| sister | | Wt | C282Y/C* | T* | | | |
| sister | | S65C/S | Wt* | T/C* | | | |
| Proband 4/81F | A2, 32; B14, 62 | S65C/S | Wt | T/C | 100 | S135 | HC + stomatocytosis |
| daughter/59" | A1, 32; B14, 15 | H63D/H, S65C/S | Wt* | T/C | 42 | 62 | |
| Control 1/28M | A2, 31; B35, 60 | S65C/S | Wt | T/C | 28 | 141 | |
| Control 2/69M | A24, 26; B8, 37 | S65C/S | Wt | T/C | 42 | 747 | 2+ |

*RE cut
**normal (15–45%)
***20—300 ng/ml (men)
2C-200 ng/ml (women)

normal iron phenotype (Table 7). Normal Control 2, who also had the HFE genotype S65C/wt, had hyperferritinemia and mildly increased stainable hepatocellular iron deposition, but had no symptoms or other objective findings attributable to iron overload (Table 7). These data indicate that S65C heterozygosity is associated with abnormal iron parameters.

EXAMPLE 7

HLA Gene Linkage

In the family of proband 1, the I105T mutation was linked to HLA-A3, B7, markers which are often linked to the C282Y mutation and its ancestral haplotype. HLA-A3, B7 is also significantly more common among C282Y-negative hemochromatosis probands than in normal control subjects tested. S65C was linked to HLA-A32 in probands 3 and 4 (and their respective families). The base-pair change in intron 4 (nt 6884T→C) was detected only in probands who inherited the S65C mutation. These data indicate that an intron 4 mutation (nt 6884→C) is a marker for chromosomes bearing the S65C HFE allele. Three of four probands who inherited mutated HFE exon 2 mutations described herein also inherited the C282Y or H63D mutations on separate chromosomes. In a fourth proband, the co-inheritance of S65C heterozygosity and hereditary stomatocytosis was associated with severe iron overload.

Altered interactions of transferrin receptor, transferrin, and C282Y and H63D mutant HFE protein contribute to the pathology of hemochromatosis. The S65C, G93R, and I105T mutations are located within the α1 domain: in the α1 helix of the HFE class I-like heavy chain (I105T and G93R), and at the tip of the A chain loop of the β-pleated sheet (S65C). These mutations affect the overall structure of the HFE gene product, and specifically affect the salt bridge between residues H63 and D95. The I105T substitution also inhibits proper folding of the α1 domain of the HFE gene product, and specifically affects the hydrophobicity of the hydrophobic F pocket.

Other embodiments are within the following claims.

What is claimed is:

1. A method of diagnosing an iron disorder or a genetic susceptibility to developing said disorder in a mammal, comprising determining the presence of a mutation in exon 2 of an HFE nucleic acid in a biological sample from said mammal, wherein said mutation is not a C→G substitution at nucleotide 187 of SEQ ID NO:1 and wherein the presence of said mutation is indicative of said disorder or a genetic susceptibility to developing said disorder.

2. The method of claim 1, wherein said disorder is hemochromatosis.

3. The method of claim 1, wherein said nucleic acid is a DNA molecule.

4. The method of claim 1, wherein said nucleic acid is a RNA molecule.

5. The method of claim 1, wherein said mutation is a missense mutation at nucleotide 314 of SEQ ID NO:1.

6. The method of claim 5, wherein said mutation is 314C.

7. The method of claim 6, wherein said mutation results in expression of mutant HFE gene product I105T.

8. The method of claim 1, wherein said mutation is at nucleotide 277 of SEQ ID NO:1.

9. The method of claim 8, wherein said mutation is 277C.

10. The method of claim 9, wherein said mutation results in expression of mutant HFE gene product G93R.

11. The method of claim 1, wherein said mutation is at nucleotide 193 of SEQ ID NO:1.

12. The method of claim 11, wherein said mutation is 193T.

13. The method of claim 12, wherein said mutation results in expression of mutant HFE gene product S65C.

14. The method of claim 1, wherein said biological sample is selected from the group consisting of whole blood, cord blood, serum, saliva, plasma, effusions, ascites, urine, stool, buccal tissue, liver tissue, kidney tissue, cerebrospinal fluid, skin, hair and tears.

15. The method of claim 14, wherein said biological sample is whole blood.

16. The method of claim 14, wherein said biological sample is saliva.

17. The method of claim 14, wherein said biological sample is hair.

18. The method of claim 1, wherein said mammal is a human.

19. The method of claim 1, further comprising amplifying said nucleic acid using a first oligonucleotide primer which is 5' to exon 2 and a second oligonucleotide primer is 3' to exon 2.

20. The method of claim 1, further comprising amplifying said nucleic acid using a first oligonucleotide primer which is 5' to nucleotide 314 of SEQ ID NO:1 and a second oligonucleotide primer which is 3' to nucleotide 314 of SEQ ID NO:1.

21. The method of claim 1, further comprising amplifying said nucleic acid using a first oligonucleotide primer which is 5' to nucleotide 277 of SEQ ID NO:1 and a second oligonucleotide primer which is 3' to nucleotide 277 of SEQ ID NO:1.

22. The method of claim 1, further comprising amplifying said nucleic acid using a first oligonucleotide primer which is 5' to nucleotide 193 of SEQ ID NO:1 and a second oligonucleotide primer which is 3' to nucleotide 193 of SEQ ID NO:1.

23. The method of claim 20, 21, or 22, wherein said first oligonucleotide primer has a nucleotide sequence of SEQ ID NO:3 and said second oligonucleotide primer has a nucleotide sequence of SEQ ID NO:4.

24. The method of claim 20, 21, or 22, wherein said first oligonucleotide primer has a nucleotide sequence of SEQ ID NO:15 and said second oligonucleotide primer has a nucleotide sequence of SEQ ID NO:16.

25. A method of diagnosing an iron disorder or a genetic susceptibility to developing said disorder in a mammal, comprising determining the presence or absence of a mutation in an intron of HFE genomic DNA in a biological sample from said mammal, wherein the presence of said mutation is indicative of said disorder or a genetic susceptibility to developing said disorder.

26. The method of claim 25, wherein said mutation is in intron 4.

27. The method of claim 26, wherein said mutation is at nucleotide 6884 of SEQ ID NO:27.

28. The method of claim 27, wherein said mutation is 6884C.

29. The method of claim 25, wherein said mutation is in intron 5.

30. The method of claim 29, wherein said mutation is at nucleotide 7055 of SEQ ID NO:27.

31. The method of claim 30, wherein said mutation is 7055G.

32. The method of claim 25, further comprising amplifying said nucleic acid using a first oligonucleotide primer which is 5' to intron 4 and a second oligonucleotide primer which is 3' to intron 4.

33. The method of claim 25, further comprising amplifying said nucleic acid using a first oligonucleotide primer which is 5' to intron 5 and a second oligonucleotide primer which is 3' to intron 5.

34. A method of diagnosing an iron disorder or a genetic susceptibility to developing said disorder in a mammal, comprising determining the presence of a mutation in a HFE gene product in a biological sample from said mammal, wherein said mutation results in a decrease in an intramolecular salt bridge formation in said HFE gene product but is not amino acid substitution H63D, and wherein the presence of said mutation is indicative of said disorder or a genetic susceptibility to developing said disorder.

35. The method of claim 34, wherein said disorder is hemochromatosis.

36. The method of claim 34, wherein said mutation is between amino acids 23–113, inclusive, of SEQ ID NO:2.

37. The method of claim 34, wherein said mutation is between amino acids 58–68, inclusive, of SEQ ID NO:2.

38. The method of claim 34, wherein said mutation is between amino acids 60–65, inclusive, of SEQ ID NO:2.

39. The method of claim 34, wherein said mutation is amino acid substitution S65C.

40. The method of claim 34, wherein said mutation is between amino acids 90–100, inclusive, of SEQ ID NO:2.

41. The method of claim 34, wherein said mutation is between amino acids 92–97, inclusive, of SEQ ID NO:2.

42. The method of claim 34, wherein said mutation is amino acid substitution G93R.

43. The method of claim 34, wherein said mutation is at amino acid 95 of SEQ ID NO:2.

44. The method of claim 34, wherein said mutation is detected by immunoassay.

45. A method of diagnosing an iron disorder or a genetic susceptibility to developing said disorder in a mammal, comprising determining the presence of a mutation in a HFE gene product in a biological sample from said mammal, said mutation being located in the α1 helix of said HFE gene product, wherein the presence of said mutation is indicative of said disorder or a genetic susceptibility to developing said disorder.

46. The method of claim 45, wherein said mutation is between amino acids 80–108, inclusive, of SEQ ID NO:2.

47. The method of claim 45, wherein said mutation is I105T.

48. The method of claim 45, wherein said mutation is G93R.

49. An isolated nucleic acid molecule encoding an HFE polypeptide comprising amino acid substitution I105T or the complement thereof.

50. An isolated nucleic acid molecule encoding an HFE polypeptide comprising amino acid substitution G93R or the complement thereof.

51. An isolated nucleic acid molecule encoding an HFE polypeptide comprising amino acid substitution S65C or the complement thereof.

52. A kit for detecting a nucleotide polymorphism associated with an iron disorder or a genetic susceptibility to developing said disorder in a mammal comprising the nucleic acid molecule of claims 49, 50, or 51.

53. A kit for the detection of the presence of a mutation in exon 2 of an HFE nucleic acid comprising a first oligonucleotide primer which is 5' to exon 2 and a second oligonucleotide primer is 3' to exon 2.

* * * * *

SEQUENCE LISTING

<160> NUMBER OF SEQ ID NOS: 30

<210> SEQ ID NO 1
<211> LENGTH: 2506
<212> TYPE: DNA
<213> ORGANISM: Homo Sapiens
<220> FEATURE:
<221> NAME/KEY: mutation
<222> LOCATION: (0)...(0)
<223> OTHER INFORMATION: Missense mutation at nucleotide 314

<400> SEQUENCE: 1

```
atgggcccgc gagccaggcc ggcgcttctc ctcctgatgc ttttgcagac cgcggtcctg      60 cagggcgct  tgctgcgttc acactctctg cactacctct tcatgggtgc ctcagagcag     120
gaccttggtc tttccttgtt tgaagctttg ggctacgtgg atgaccagct gttcgtgttc     180
tatgatcatg agagtcgccg tgtggagccc cgaactccat gggtttccag tagaatttca     240
agccagatgt ggctgcagct gagtcagagt ctgaaagggt gggatcacat gttcactgtt     300
gacttctgga ctattatgga aaatcacaac cacagcaagg agtcccacac cctgcaggtc     360
```

```
atcctgggct gtgaaatgca agaagacaac agtaccgagg gctactggaa gtacgggtat    420
gatgggcagg accaccttga attctgccct gacacactgg attggagagc agcagaaccc    480
agggcctggc ccaccaagct ggagtgggaa aggcacaaga ttcgggccag gcagaacagg    540
gcctacctgg agagggactg ccctgcacag ctgcagcagt tgctggagct ggggagaggt    600
gttttggacc aacaagtgcc tcctttggtg aaggtgacac atcatgtgac ctcttcagtg    660
accactctac ggtgtcgggc cttgaactac taccccagaa acatcaccat gaagtggctg    720
aaggataagc agccaatgga tgccaaggag ttcgaaccta agacgtatt  gcccaatggg    780 gatgggacct accagggctg ataaccttgc gctgtacccc ctggggaaga gcagagatat    840
acgtgccagg tggagcaccc aggcctggat cagcccctca ttgtgatctg ggagccctca    900
ccgtctggca ccctagtcat tggagtcatc agtggaattg ctgttttgt cgtcatcttg     960 ttcattggaa ttttgttcat aatattaagg aagaggcagg gttcaagagg agccatgggg   1020
cactacgtct tagctgaacg tgagtgacac gcagcctgca gactcactgt gggaaggaga   1080
caaaactaga gactcaaaga gggagtgcat ttatgagctc ttcatgtttc aggagagagt   1140
tgaacctaaa catagaaatt gcctgacgaa ctccttgatt ttagccttct ctgttcattt   1200
cctcaaaaag atttccccat ttaggtttct gagttcctgc atgccggtga tcccctagctg  1260 tgacctctcc cctggaactg tctctcatga acctcaagct gcatctagag gcttccttca   1320
tttcctccgt cacctcagag acatacacct atgtcatttc atttcctatt tttggaagag   1380
gactccttaa atttggggga cttacatgat tcattttaac atctgagaaa agctttgaac   1440
cctgggacgt ggctagtcat aaccttacca gattttttaca catgtatcta tgcattttct   1500
ggacccgttc aacttttcct ttgaatcctc tctctgtgtt acccagtaac tcatctgtca   1560
ccaagccttg gggattcttc catctgattg tgatgtgagt tgcacagcta tgaaggctgt   1620
gcactgcacg aatggaagag gcacctgtcc cagaaaaagc atcatggcta tctgtgggta   1680
gtatgatggg tgttttttagc aggtaggagg caaatatctt gaaagggggtt gtgaagaggt   1740 gtttttttcta attggcatga aggtgtcata cagatttgca aagtttaatg gtgccttcat   1800
ttgggatgct actctagtat tccagacctg aagaatcaca ataattttct acctggtctc   1860
tccttgttct gataatgaaa attatgataa ggatgataaa agcacttact tcgtgtccga   1920
ctcttctgag cacctactta catgcattac tgcatgcact tcttacaata attctatgag   1980
ataggtacta ttatccccat ttcttttta aatgaagaaa gtgaagtagg ccgggcacgg    2040
tggctcgcgc ctgtggtccc agggtgctga gattgcaggt gtgagccacc ctgcccagcc   2100
gtcaaaagag tcttaatata tatatccaga tggcatgtgt ttactttatg ttactacatg   2160
cacttggctg cataaatgtg gtacaaccat tctgtcttga agggcaggtg cttcaggata   2220
ccatatacag ctcagaagtt tcttctttag gcattaaatt ttagcaaaga tatctcatct   2280
cttcttttaa accattttct ttttttgtgg ttagaaaagt tatgtagaaa aaagtaaatg   2340
tgatttacgc tcattgtaga aaagctataa aatgaataca attaaagctg ttatttaatt   2400
agccagtgaa aaactattaa caacttgtct attacctgtt agtattattg ttgcattaaa   2460
aatgcatata ctttaataaa tgtacattgt attgtaaaaa aaaaaa                  2506

<210> SEQ ID NO 2
<211> LENGTH: 348
<212> TYPE: PRT
<213> ORGANISM: Homo Sapiens
```

<400> SEQUENCE: 2

```
Met Gly Pro Arg Ala Arg Pro Ala Leu Leu Leu Met Leu Leu Gln
 1               5                  10                  15

Thr Ala Val Leu Gln Gly Arg Leu Leu Arg Ser His Ser Leu His Tyr
            20                  25                  30

Leu Phe Met Gly Ala Ser Glu Gln Asp Leu Gly Leu Ser Leu Phe Glu
        35                  40                  45

Ala Leu Gly Tyr Val Asp Asp Gln Leu Phe Val Phe Tyr Asp His Glu
    50                  55                  60

Ser Arg Arg Val Glu Pro Arg Thr Pro Trp Val Ser Ser Arg Ile Ser
65                  70                  75                  80

Ser Gln Met Trp Leu Gln Leu Ser Gln Ser Leu Lys Gly Trp Asp His
                85                  90                  95

Met Phe Thr Val Asp Phe Trp Thr Ile Met Glu Asn His Asn His Ser
            100                 105                 110

Lys Glu Ser His Thr Leu Gln Val Ile Leu Gly Cys Glu Met Gln Glu
        115                 120                 125

Asp Asn Ser Thr Glu Gly Tyr Trp Lys Tyr Gly Tyr Asp Gly Gln Asp
    130                 135                 140

His Leu Glu Phe Cys Pro Asp Thr Leu Asp Trp Arg Ala Ala Glu Pro
145                 150                 155                 160

Arg Ala Trp Pro Thr Lys Leu Glu Trp Glu Arg His Lys Ile Arg Ala
                165                 170                 175

Arg Gln Asn Arg Ala Tyr Leu Glu Arg Asp Cys Pro Ala Gln Leu Gln
            180                 185                 190

Gln Leu Leu Glu Leu Gly Arg Gly Val Leu Asp Gln Gln Val Pro Pro
        195                 200                 205

Leu Val Lys Val Thr His His Val Thr Ser Ser Val Thr Thr Leu Arg
    210                 215                 220

Cys Arg Ala Leu Asn Tyr Tyr Pro Gln Asn Ile Thr Met Lys Trp Leu
225                 230                 235                 240

Lys Asp Lys Gln Pro Met Asp Ala Lys Glu Phe Glu Pro Lys Asp Val
                245                 250                 255

Leu Pro Asn Gly Asp Gly Thr Tyr Gln Gly Trp Ile Thr Leu Ala Val
            260                 265                 270

Pro Pro Gly Glu Glu Gln Arg Tyr Thr Cys Gln Val Glu His Pro Gly
        275                 280                 285

Leu Asp Gln Pro Leu Ile Val Ile Trp Glu Pro Ser Pro Ser Gly Thr
    290                 295                 300

Leu Val Ile Gly Val Ile Ser Gly Ile Ala Val Phe Val Val Ile Leu
305                 310                 315                 320

Phe Ile Gly Ile Leu Phe Ile Ile Leu Arg Lys Arg Gln Gly Ser Arg
                325                 330                 335

Gly Ala Met Gly His Tyr Val Leu Ala Glu Arg Glu
            340                 345
```

<210> SEQ ID NO 3
<211> LENGTH: 23
<212> TYPE: DNA
<213> ORGANISM: Artificial Sequence
<220> FEATURE:
<223> OTHER INFORMATION: Primer

<400> SEQUENCE: 3
cctcctacta cacatggtta agg        23

<210> SEQ ID NO 4
<211> LENGTH: 21
<212> TYPE: DNA
<213> ORGANISM: Artificial Sequence
<220> FEATURE:
<223> OTHER INFORMATION: Reverse Primer

<400> SEQUENCE: 4
gctctgacaa cctcaggaag g    21

<210> SEQ ID NO 5
<211> LENGTH: 22
<212> TYPE: DNA
<213> ORGANISM: Artificial Sequence
<220> FEATURE:
<223> OTHER INFORMATION: Primer

<400> SEQUENCE: 5
ggtggaaata gggacctatt cc    22

<210> SEQ ID NO 6
<211> LENGTH: 22
<212> TYPE: DNA
<213> ORGANISM: Artificial Sequence
<220> FEATURE:
<223> OTHER INFORMATION: Reverse Primer

<400> SEQUENCE: 6
cactctgcca ctagactata gg    22

<210> SEQ ID NO 7
<211> LENGTH: 21
<212> TYPE: DNA
<213> ORGANISM: Artificial Sequence
<220> FEATURE:
<223> OTHER INFORMATION: Primer

<400> SEQUENCE: 7
gttccagtct tcctggcaag g    21

<210> SEQ ID NO 8
<211> LENGTH: 22
<212> TYPE: DNA
<213> ORGANISM: Artificial Sequence
<220> FEATURE:
<223> OTHER INFORMATION: Reverse Primer

<400> SEQUENCE: 8
aaatgcttcc catggatgcc ag    22

<210> SEQ ID NO 9
<211> LENGTH: 30
<212> TYPE: DNA
<213> ORGANISM: Artificial Sequence
<220> FEATURE:
<223> OTHER INFORMATION: Primer

<400> SEQUENCE: 9
aaaggatcca ccatgggccc gcgagccagg    30

<210> SEQ ID NO 10
<211> LENGTH: 20
<212> TYPE: DNA
<213> ORGANISM: Artificial Sequence
<220> FEATURE:

<223> OTHER INFORMATION: Reverse Primer

<400> SEQUENCE: 10
gtgagtctgc aggctgcgtg                                                           20

<210> SEQ ID NO 11
<211> LENGTH: 21
<212> TYPE: DNA
<213> ORGANISM: Artificial Sequence
<220> FEATURE:
<223> OTHER INFORMATION: Primer

<400> SEQUENCE: 11
gttccagtct tcctggcaag g                                                         21

<210> SEQ ID NO 12
<211> LENGTH: 22
<212> TYPE: DNA
<213> ORGANISM: Artificial Sequence
<220> FEATURE:
<223> OTHER INFORMATION: Reverse Primer

<400> SEQUENCE: 12
aaatgcttcc catggatgcc ag                                                        22

<210> SEQ ID NO 13
<211> LENGTH: 21
<212> TYPE: DNA
<213> ORGANISM: Artificial Sequence
<220> FEATURE:
<223> OTHER INFORMATION: Primer

<400> SEQUENCE: 13
gttccagtct tcctggcaag g                                                         21

<210> SEQ ID NO 14
<211> LENGTH: 22
<212> TYPE: DNA
<213> ORGANISM: Artificial Sequence
<220> FEATURE:
<223> OTHER INFORMATION: Reverse Primer

<400> SEQUENCE: 14
aaatgcttcc catggatgcc ag                                                        22

<210> SEQ ID NO 15
<211> LENGTH: 21
<212> TYPE: DNA
<213> ORGANISM: Artificial Sequence
<220> FEATURE:
<223> OTHER INFORMATION: Primer

<400> SEQUENCE: 15
gtgtggagcc tcaacatcct g                                                         21

<210> SEQ ID NO 16
<211> LENGTH: 21
<212> TYPE: DNA
<213> ORGANISM: Artificial Sequence
<220> FEATURE:
<223> OTHER INFORMATION: Reverse Primer

<400> SEQUENCE: 16
acaagacctc agacttccag c                                                         21

```
<210> SEQ ID NO 17
<211> LENGTH: 22
<212> TYPE: DNA
<213> ORGANISM: Artificial Sequence
<220> FEATURE:
<223> OTHER INFORMATION: Primer

<400> SEQUENCE: 17
ggtggaaata gggacctatt cc                                                22

<210> SEQ ID NO 18
<211> LENGTH: 22
<212> TYPE: DNA
<213> ORGANISM: Artificial Sequence
<220> FEATURE:
<223> OTHER INFORMATION: Reverse Primer

<400> SEQUENCE: 18
cactctgcca ctagagtata gg                                                22

<210> SEQ ID NO 19
<211> LENGTH: 21
<212> TYPE: DNA
<213> ORGANISM: Artificial Sequence
<220> FEATURE:
<223> OTHER INFORMATION: Primer

<400> SEQUENCE: 19
gttccagtct tcctggcaag g                                                 21

<210> SEQ ID NO 20
<211> LENGTH: 21
<212> TYPE: DNA
<213> ORGANISM: Artificial Sequence
<220> FEATURE:
<223> OTHER INFORMATION: Reverse Primer

<400> SEQUENCE: 20
ttacctcctc aggcactcct c                                                 21

<210> SEQ ID NO 21
<211> LENGTH: 30
<212> TYPE: DNA
<213> ORGANISM: Artificial Sequence
<220> FEATURE:
<223> OTHER INFORMATION: Primer

<400> SEQUENCE: 21
aaaggatcca ccatgggccc gcgagccagg                                        30

<210> SEQ ID NO 22
<211> LENGTH: 20
<212> TYPE: DNA
<213> ORGANISM: Artificial Sequence
<220> FEATURE:
<223> OTHER INFORMATION: Reverse Primer

<400> SEQUENCE: 22
gtgagtctgc aggctgcgtg                                                   20

<210> SEQ ID NO 23
<211> LENGTH: 21
<212> TYPE: DNA
<213> ORGANISM: Artificial Sequence
<220> FEATURE:
<223> OTHER INFORMATION: Primer
```

-continued

```
<400> SEQUENCE: 23
tgcctgagga ggtaattatg g                                              21

<210> SEQ ID NO 24
<211> LENGTH: 22
<212> TYPE: DNA
<213> ORGANISM: Artificial Sequence
<220> FEATURE:
<223> OTHER INFORMATION: Reverse Primer

<400> SEQUENCE: 24
aaatgcttcc catggatgcc ag                                             22

<210> SEQ ID NO 25
<211> LENGTH: 21
<212> TYPE: DNA
<213> ORGANISM: Artificial Sequence
<220> FEATURE:
<223> OTHER INFORMATION: Primer

<400> SEQUENCE: 25
tgcctgagga ggtaattatg g                                              21

<210> SEQ ID NO 26
<211> LENGTH: 22
<212> TYPE: DNA
<213> ORGANISM: Artificial Sequence
<220> FEATURE:
<223> OTHER INFORMATION: Reverse Primer

<400> SEQUENCE: 26
aaatgcttcc catggatgcc ag                                             22

<210> SEQ ID NO 27
<211> LENGTH: 12146
<212> TYPE: DNA
<213> ORGANISM: Homo Sapiens

<400> SEQUENCE: 27
ggatccttta accgaggaga ttattatagc cggagctctg aagcagcaat ctcagttctt     60
gtgatagtga gcaaagaact acaaactaac accaaaatgc aagcttaaag caaagttttat   120 tgaagcacaa taatacactc tgagggacag cgggcttatt tctgcgaagt gaactcagca   180
cttctttaca gagctcaagg tgcttttatg gggtttgtgg ggaggagttg aggttttggc   240
tgtatctgag tgacaggatg atgttatttg attgaagttt atagctatac aatctaaaat   300
taaactgtgc atggtcttac ctataatttg ttaagaaaag cctcccaggg atgggggggc   360
aaaactgtat gtaaattcta ttataatgat ggcatgatga acttggggtg aacttgaaga   420
caggcttttg tgttgttggg catgtgccac cttagggaat ttccacctgt accctccttt   480
ctctttctcc aggatatttt ggccacagac tttatcataa actccatccc ttagggtggc   540
attagggtag tcttgggcct gaatttaggt gggccagtgg ctgtcttagt gacagccttt   600
ccgctctctt ctgtcatccc ctcccaactg ctaatgtcta actacctaac aattacccat   660
taaatcagtg tgtctggggt taggagcagg cctcaatatg tttaatcatt ctccagataa   720
tcccaatact gtaaagtttg tgaaacactt gtcagataat tcaattatga aggctgtgga   780
acgtgtttca gtaggatcta attggttaat gttatgactt aattaatttg aatcaaaaaa   840
caaaatgaaa aagcttttata tttctaagtc aaataagaca taagttggtc taaggttgag   900
ataaaatttt taaatgtatg attgaattttt gaaaatcata aatatttaaa tatctaaagt   960
```

```
tcagatcaga acattgcgaa gctactttcc ccaatcaaca acaccccttc aggatttaaa    1020
aaccaagggg gacactggat cacctagtgt tcacaagca ggtaccttct gctgtaggag    1080
agagagaact aaagttctga aagacctgtt gcttttcacc aggaagtttt actgggcatc    1140
tcctgagcct aggcaatagc tgtagggtga cttctggagc catcccgtt tccccgcccc    1200 ccaaaagaag cggagattta acgggacgt gcggccagag ctggggaaat gggcccgcga    1260
gccaggccgg cgcttctcct cctgatgctt ttgcagaccg cggtcctgca ggggcgcttg    1320
ctgcgtgagt ccgagggctg cgggcgaact aggggcgcgg cggggtgga aaaatcgaaa    1380 ctagcttttt ctttgcgctt gggagtttgc taactttgga ggacctgctc aacccaatcc    1440
gcaagcccct ctccctactt tctgcgtcca gaccccgtga gggagtgcct accactgaac    1500
tgcagatagg ggtccctcgc cccaggacct gcccctccc ccggctgtcc cggctctgcg    1560
gagtgacttt tggaaccgcc cactcccttc ccccaactag aatgctttta aataaatctc    1620
gtagttcctc acttgagctg agctaagcct ggggctcctt gaacctggaa ctcgggttta    1680
tttccaatgt cagctgtgca gttttttccc cagtcatctc caaacaggaa gttcttccct    1740
gagtgcttgc cgagaaggct gagcaaaccc acagcaggat ccgcacgggg tttccacctc    1800
agaacgaatg cgttgggcgg tggggcgcg aaagagtggc gttggggatc tgaattcttc    1860
accattccac ccacttttgg tgagacctgg ggtggaggtc tctagggtgg gaggctcctg    1920
agagaggcct acctcgggcc tttccccact cttggcaatt gttcttttgc ctggaaaatt    1980
aagtatatgt tagttttgaa cgtttgaact gaacaattct cttttcggct aggctttatt    2040
gatttgcaat gtgctgtgta attaagaggc ctctctacaa agtactgata atgaacatgt    2100
aagcaatgca ctcacttcta agttacattc atatctgatc ttatttgatt ttcactaggc    2160 ataggaggt aggagctaat aatacgttta ttttactaga agttaactgg aattcagatt    2220
atataactct tttcaggtta caaagaacat aaataatctg gttttctgat gttatttcaa    2280
gtactacagc tgcttctaat cttagttgac agtgattttg ccctgtagtg tagcacagtg    2340
ttctgtgggt cacacgccgg cctcagcaca gcactttgag ttttggtact acgtgtatcc    2400
acattttaca catgacaaga atgaggcatg gcacggcctg cttcctggca aatttattca    2460
atggtacacg gggctttggt ggcagagctc atgtctccac ttcatagcta tgattcttaa    2520
acatcacact gcattagagg ttgaataata aaatttcatg ttgagcagaa atattcattg    2580
tttacaagtg taaatgagtc ccagccatgt gttgcactgt tcaagcccca agggagagag    2640
cagggaaaca agtctttacc ctttgatatt ttgcattcta gtgggagaga tgacaataag    2700
caaatgagca gaaagatata caacatcagg aaatcatggg tgttgtgaga agcagagaag    2760
tcagggcaag tcactctggg gctgacactt gagcagagac atgaaggaaa taagaatgat    2820
attgactggg agcagtattt cccaggcaaa ctgagtgggc ctggcaagtt ggattaaaaa    2880
gcgggttttc tcagcactac tcatgtgtgt gtgtgtgggg gggggcgg cgtgggggtg    2940 ggaagggga ctaccatctg catgtaggat gtctagcagt atcctgtcct ccctactcac    3000
taggtgctag gagcactccc ccagtcttga caaccaaaaa tgtctctaaa ctttgccaca    3060
tgtcacctag tagacaaact cctggttaag aagctcgggt tgaaaaaaat aaacaagtag    3120
tgctggggag tagaggccaa gaagtaggta atgggctcag aagaggagcc acaaacaagg    3180
ttgtgcaggc gcctgtaggc tgtggtgtga attctagcca aggagtaaca gtgatctgtc    3240
acaggctttt aaaagattgc tctggctgct atgtggaaag cagaatgaag ggagcaacag    3300
```

-continued

```
taaaagcagg gagcccagcc aggaagctgt tacacagtcc aggcaagagg tagtggagtg      3360
ggctgggtgg gaacagaaaa gggagtgaca aaccattgtc tcctgaatat attctgaagg      3420
aagttgctga aggattctat gttgtgtgag agaaagagaa gaattggctg ggtgtagtag      3480
ctcatgccaa ggaggaggcc aaggagagca gattcctgag ctcaggagtt caagaccagc      3540
ctgggcaaca cagcaaaacc ccttctctac aaaaaataca aaaattagct gggtgtggtg      3600
gcatgcacct gtgatcctag ctactcggga ggctgaggtg gagggtattg cttgagccca      3660
ggaagttgag gctgcagtga gccatgactg tgccactgta cttcagccta ggtgacagag      3720
caagaccctg tctcccctga cccctgaaa agagaagag ttaaagttga ctttgttctt       3780
tattttaatt ttattggcct gagcagtggg gtaattggca atgccatttc tgagatggtg      3840
aaggcagagg aaagagcagt ttggggtaaa tcaaggatct gcatttggac atgttaagtt      3900
tgagattcca gtcaggcttc caagtggtga ggccacatag gcagttcagt gtaagaattc      3960
aggaccaagg cagggcacgg tggctcactt ctgtaatccc agcactttgg tggctgaggc      4020
aggtagatca tttgaggtca ggagtttgag acaagcttgg ccaacatggt gaaaccccat      4080
gtctactaaa aatacaaaaa ttagcctggt gtggtggcgc acgcctatag tcccaggttt      4140
tcaggaggct taggtaggag aatcccttga acccaggagg tgcaggttgc agtgagctga      4200
gattgtgcca ctgcactcca gcctgggtga tagagtgaga ctctgtctca aaaaaaaaa      4260 aaaaaaaaa aaaaaaaaa aactgaagga attattcctc aggatttggg tctaatttgc       4320
cctgagcacc aactcctgag ttcaactacc atggctagac acccttaac attttctaga      4380 atccaccagc tttagtggag tctgtctaat catgagtatt ggataggat ctgggggcag      4440 tgagggggtg gcagccacgt gtggcagaga aaagcacaca aggaaagagc acccaggact      4500
gtcatatgga agaagacag gactgcaact caccccttcac aaaatgagga ccagacacag      4560
ctgatggtat gagttgatgc aggtgtgtgg agcctcaaca tcctgctccc ctcctactac      4620
acatggttaa ggcctgttgc tctgtctcca ggttcacact ctctgcacta cctcttcatg      4680
ggtgcctcag agcaggacct tggtctttcc ttgtttgaag cttttgggcta cgtggatgac      4740 cagctgttcg tgttctatga tcatgagagt cgccgtgtgg agccccgaac tccatgggtt      4800
tccagtagaa tttcaagcca gatgtggctg cagctgagtc agagtctgaa agggtgggat      4860
cacatgttca ctgttgactt ctggactatt atggaaaatc acaaccacag caagggtatg      4920
tggagagggg gcctcacctt cctgaggttg tcagagcttt tcatcttttc atgcatcttg      4980
aaggaaacag ctggaagtct gaggtcttgt gggagcaggg aagagggaag gaatttgctt      5040
cctgagatca tttggtcctt ggggatggtg gaaatagggga cctattcctt tggttgcagt      5100
taacaaggct ggggattttt ccagagtccc acaccctgca ggtcatcctg ggctgtgaaa      5160
tgcaagaaga caacagtacc gagggctact ggaagtacgg gtatgatggg caggaccacc      5220
ttgaattctg ccctgacaca ctggattgga gagcagcaga acccagggcc tggcccacca      5280
agctggagtg ggaaaggcac aagattcggg ccaggcagaa cagggcctac ctggagaggg      5340
actgccctgc acagctgcag cagttgctgg agctggggag aggtgttttg gaccaacaag      5400
gtatggtgga aacacacttc tgcccctata ctctagtggc agagtggagg aggttgcagg      5460
gcacggaatc cctggttgga gtttcagagg tggctgaggc tgtgtgcctc tccaaattct      5520
gggaagggac tttctcaatc ctagagtctc taccttataa ttgagatgta tgagacagcc      5580
acaagtcatg ggtttaattt cttttctcca tgcatatggc tcaaagggaa gtgtctatgg      5640
cccttgcttt ttatttaacc aataatcttt tgtatattta tacctgttaa aaattcagaa      5700
```

-continued

| | |
|---|---|
| atgtcaaggc cgggcacggt ggctcacccc tgtaatccca gcactttggg aggccgaggc | 5760 |
| gggtggtcac aaggtcagga gtttgagacc agcctgacca acatggtgaa acccgtctct | 5820 |
| aaaaaaatac aaaaattagc tggtcacagt catgcgcacc tgtagtccca gctaattgga | 5880 |
| aggctgaggc aggagcatcg cttgaacctg ggaagcggaa gttgcactga gccaagatcg | 5940 |
| cgccactgca ctccagccta ggcagcagag tgagactcca tcttaaaaaa aaaaaaaaaa | 6000 |
| aaaaagagaa ttcagagatc tcagctatca tatgaatacc aggacaaaat atcaagtgag | 6060 |
| gccacttatc agagtagaag aatcctttag gttaaaagtt tctttcatag aacatagcaa | 6120 |
| taatcactga agctacctat cttacaagtc cgcttcttat aacaatgcct cctaggttga | 6180 |
| cccaggtgaa actgaccatc tgtattcaat cattttcaat gcacataaag gcaatttta | 6240 |
| tctatcagaa caaagaacat gggtaacaga tatgtatatt tacatgtgag gagaacaagc | 6300 |
| tgatctgact gctctccaag tgacactgtg ttagagtcca atcttaggac acaaaatggt | 6360 |
| gtctctcctg tagcttgttt ttttctgaaa agggtatttc cttcctccaa cctatagaag | 6420 |
| gaagtgaaag ttccagtctt cctggcaagg gtaaacagat cccctctcct catccttcct | 6480 |
| cttttcctgtc aagtgcctcc tttggtgaag gtgacacatc atgtgacctc ttcagtgacc | 6540 |
| actctacggt gtcgggcctt gaactactac ccccagaaca tcaccatgaa gtggctgaag | 6600 |
| gataagcagc caatggatgc caaggagttc gaacctaaag acgtattgcc caatggggat | 6660 |
| gggacctacc agggctggat aaccttggct gtaccccctg gggaagagca gagatatacg | 6720 |
| tgccaggtgg agcacccagg cctggatcag cccctcattg tgatctgggg tatgtgactg | 6780 |
| atgagagcca ggagctgaga aaatctattg ggggttgaga ggagtgcctg aggaggtaat | 6840 |
| tatggcagtg agatgaggat ctgctctttg ttaggggatg ggctgagggt ggcaatcaaa | 6900 |
| ggctttaact tgcttttct gttttagagc cctcaccgtc tggcacccta gtcattggag | 6960 |
| tcatcagtgg aattgctgtt tttgtcgtca tcttgttcat tggaattttg ttcataatat | 7020 |
| taaggaagag gcagggttca agtgagtagg aacaagggg aagtctctta gtacctctgc | 7080 |
| cccagggcac agtgggaaga ggggcagagg ggatctggca tccatgggaa gcatttttct | 7140 |
| catttatatt ctttggggac accagcagct ccctgggaga cagaaaataa tggttctccc | 7200 |
| cagaatgaaa gtctctaatt caacaaacat cttcagagca cctactattt tgcaagagct | 7260 |
| gtttaaggta gtacagggc tttgaggttg agaagtcact gtggctattc tcagaaccca | 7320 |
| aatctggtag ggaatgaaat tgatagcaag taaatgtagt taaagaagac cccatgaggt | 7380 |
| cctaaagcag gcaggaagca aatgcttagg gtgtcaaagg aaagaatgat cacattcagc | 7440 |
| tggggatcaa gatagccttc tggatcttga aggagaagct ggattccatt aggtgaggtt | 7500 |
| gaagatgatg ggaggtctac acagacggag caaccatgcc aagtaggaga gtataaggca | 7560 |
| tactgggaga ttagaaataa ttactgtacc ttaaccctga gtttgcttag ctatcactca | 7620 |
| ccaattatgc atttctaccc cctgaacatc tgtggtgtag ggaaagaga atcagaaaga | 7680 |
| agccagctca tacagagtcc aagggtcttt tgggatattg ggttatgatc actgggtgt | 7740 |
| cattgaagga tcctaagaaa ggaggaccac gatctcccctt atatggtgaa tgtgttgtta | 7800 |
| agaagttaga tgagaggtga ggagaccagt tagaaagcca ataagcattt ccagatgaga | 7860 |
| gataatggtt cttgaaatcc aatagtgccc aggtctaaat tgagatgggt gaatgaggaa | 7920 |
| aataaggaag agaagagagg caagatggtg cctaggtttg tgatgcctct ttcctgggtc | 7980 |
| tcttgtctcc acaggaggag ccatggggca ctacgtctta gctgaacgtg agtgacacgc | 8040 |

-continued

```
agcctgcaga ctcactgtgg gaaggagaca aaactagaga ctcaaagagg gagtgcattt    8100
atgagctctt catgtttcag gagagagttg aacctaaaca tagaaattgc ctgacgaact    8160
ccttgatttt agccttctct gttcatttcc tcaaaaagat ttccccattt aggtttctga    8220
gttcctgcat gccggtgatc cctagctgtg acctctcccc tggaactgtc tctcatgaac    8280
ctcaagctgc atctagaggc ttccttcatt tcctccgtca cctcagagac atacacctat    8340
gtcatttcat ttcctatttt tggaagagga ctccttaaat ttgggggact tacatgattc    8400
attttaacat ctgagaaaag ctttgaaccc tgggacgtgg ctagtcataa ccttaccaga    8460
tttttacaca tgtatctatg catttctgg acccgttcaa cttttccttt gaatcctctc    8520
tctgtgttac ccagtaactc atctgtcacc aagccttggg gattcttcca tctgattgtg    8580
atgtgagttg cacagctatg aaggctgtac actgcacgaa tggaagaggc acctgtccca    8640
gaaaaagcat catggctatc tgtgggtagt atgatgggtg ttttagcag gtaggaggca    8700 aatatcttga aaggggttgt gaagaggtgt tttttctaat tggcatgaag gtgtcataca    8760
gatttgcaaa gtttaatggt gccttcattt gggatgctac tctagtattc cagacctgaa    8820
gaatcacaat aattttctac ctggtctctc cttgttctga taatgaaaat tatgataagg    8880
atgataaaag cacttacttc gtgtccgact cttctgagca cctacttaca tgcattactg    8940
catgcacttc ttacaataat tctatgagat aggtactatt atccccattt ctttttaaa    9000 tgaagaaagt gaagtaggcc gggcacggtg gctcacgcct gtaatcccag cactttggga    9060
ggccaaagcg ggtggatcac gaggtcagga gatcgagacc atcctggcta acatggtgaa    9120
accccatctc taataaaaat acaaaaaatt agctgggcgt ggtggcagac gcctgtagtc    9180
ccagctactc ggaaggctga ggcaggagaa tggcatgaac ccaggaggca gagcttgcag    9240
tgagccgagt ttgcgccact gcactccagc ctaggtgaca gagtgagact ccatctcaaa    9300
aaaataaaaa taaaataaa aaatgaaaa aaaaagaaa gtgaagtata gagtatctca    9360
tagtttgtca gtgatagaaa caggtttcaa actcagtcaa tctgaccgtt tgatacatct    9420
cagacaccac tacattcagt agtttagatg cctagaataa atagagaagg aaggagatgg    9480
ctcttctctt gtctcattgt gtttcttctg aatgagcttg aatcacatga agggaacag    9540 cagaaaacaa ccaactgatc ctcagctgtc atgtttcctt taaagtccc tgaaggaagg    9600 tcctggaatg tgactcctt gctcctctgt tgctctcttt ggcattcatt tctttggacc    9660
ctacgcaagc actgtaattg gtggggacag ctagtggccc tgctgggctt cacacacggt    9720
gtcctcccta ggccagtgcc tctggagtca gaactctggt ggtatttccc tcaatgaagt    9780
ggagtaagct ctctcatttt gagatggtat aatggaagcc accaagtggc ttagaggatg    9840
cccaggtcct tccatggagc cactggggtt ccggtgcaca ttaaaaaaaa aatctaacca    9900
ggacattcag gaattgctag attctgggaa atcagttcac catgttcaaa agagtctttt    9960
tttttttttt gagactctat tgcccaggct ggagtgcaat ggcatgatct cggctcactg    10020
taacctctgc ctcccaggtt caagcgattc tcctgtctca gcctcccaag tagctgggat    10080
tacaggcgtg caccaccatg cccggctaat ttttgtattt ttagtagaga cagggtttca    10140
ccatgttggc caggctggtc tcgaactctc ctgacctcgt gatccgcctg cctcggcctc    10200
ccaaagtgct gagattacag gtgtgagcca ccctgcccag ccgtcaaaag agtcttaata    10260
tatatatcca gatggcatgt gtttacttta tgttactaca tgcacttggc tgcataaatg    10320
tggtacaagc attctgtctt gaagggcagg tgcttcagga taccatatac agctcagaag    10380
tttcttcttt aggcattaaa ttttagcaaa gatatctcat ctcttctttt aaaccatttt    10440
```

-continued

```
cttttttttgt ggttagaaaa gttatgtaga aaaagtaaaa tgtgatttac gctcattgta    10500
gaaaagctat aaaatgaata caattaaagc tgttatttaa ttagccagtg aaaaactatt    10560
aacaacttgt ctattacctg ttagtattat tgttgcatta aaaatgcata tactttaata    10620
aatgtacatt gtattgtata ctgcatgatt ttattgaagt tcttgttcat cttgtgtata    10680
tacttaatcg ctttgtcatt ttggagacat ttattttgct tctaatttct ttacattttg    10740
tcttacggaa tattttcatt caactgtggt agccgaatta atcgtgtttc ttcactctag    10800
ggacattgtc gtctaagttg taagacattg gttattttac cagcaaacca ttctgaaagc    10860
atatgacaaa ttatttctct cttaatatct tactatactg aaagcagact gctataaggc    10920
ttcacttact cttctacctc ataaggaata tgttacaatt aatttattag gtaagcattt    10980
gttttatatt ggttttattt cacctgggct gagatttcaa gaaacacccc agtcttcaca    11040
gtaacacatt tcactaacac atttactaaa catcagcaac tgtggcctgt taatttttt    11100 aatagaaatt ttaagtcctc attttctttc ggtgtttttt aagcttaatt tttctggctt    11160
tattcataaa ttcttaaggt caactacatt tgaaaaatca aagacctgca ttttaaattc    11220
ttattcacct ctggcaaaac cattcacaaa ccatggtagt aaagagaagg gtgacacctg    11280
gtggccatag gtaaatgtac cacggtggtc cggtgaccag agatgcagcg ctgagggttt    11340
tcctgaaggt aaaggaataa agaatgggtg gaggggcgtg cactggaaat cacttgtaga    11400
gaaaagcccc tgaaatttg agaaaacaaa caagaaacta cttaccagct atttgaattg    11460
ctggaatcac aggccattgc tgagctgcct gaactgggaa cacaacagaa ggaaaacaaa    11520
ccactctgat aatcattgag tcaagtacag caggtgattg aggactgctg agaggtacag    11580
gccaaaattc ttatgttgta ttataataat gtcatcttat aatactgtca gtattttata    11640
aaacattctt cacaaactca cacacattta aaaacaaaac actgtctcta aaatccccaa    11700 attttcata aactcagttt taaactaact ttttttcaaa ccacaatctg atttaacaat    11760
gactatcatt taaatatttc tgactttcaa attaaagatt ttcacatgca ggctgatatt    11820
tgtaattgtg attctctctg taggctttgg gtataatgtg ttcttttcct tttttgcatc    11880
agcgattaac ttctacactc taacatgtag aatgttacta caatattaaa gtattttgta    11940
tgacaatttt atttgaaagc ctaggatgcg ttgacatcct gcatgcattt attacttgat    12000
atgcatgcat tctggtatct caagcattct atttctgagt aattgtttaa ggtgtagaag    12060
agatagatat ggtggatttg gagttgatac ttatatattt tctatttctt ggatggatga    12120
atttgtacat taaagttttt ccatgg                                          12146
```

<210> SEQ ID NO 28
<211> LENGTH: 17
<212> TYPE: DNA
<213> ORGANISM: Artificial Sequence
<220> FEATURE:
<223> OTHER INFORMATION: G93R Mutation

<400> SEQUENCE: 28

```
gtctgaaacg gtgggat                                                        17
```

<210> SEQ ID NO 29
<211> LENGTH: 18
<212> TYPE: DNA
<213> ORGANISM: Artificial Sequence
<220> FEATURE:
<223> OTHER INFORMATION: I105T Mutation -continued

```
<400> SEQUENCE: 29
acttctggac tactatgg                                                          18

<210> SEQ ID NO 30
<211> LENGTH: 17
<212> TYPE: DNA
<213> ORGANISM: Artificial Sequence
<220> FEATURE:
<223> OTHER INFORMATION: S65C Mutation

<400> SEQUENCE: 30
atcatgagtg tcgccgt                                                           17
```